(12) United States Patent
Okihara

(10) Patent No.: US 9,533,103 B2
(45) Date of Patent: Jan. 3, 2017

(54) PREFILLED SYRINGE

(75) Inventor: Hitoshi Okihara, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 1036 days.

(21) Appl. No.: 13/621,112

(22) Filed: Sep. 15, 2012

(65) Prior Publication Data

US 2013/0012888 A1    Jan. 10, 2013

Related U.S. Application Data

(63) Continuation of application No. PCT/JP2010/073733, filed on Dec. 28, 2010.

(30) Foreign Application Priority Data

Mar. 29, 2010   (JP) .................................. 2010-076389

(51) Int. Cl.
    *A61M 5/315*        (2006.01)
    *A61M 5/31*          (2006.01)

(52) U.S. Cl.
    CPC .. *A61M 5/31515* (2013.01); *A61M 2005/3104* (2013.01); *A61M 2005/3118* (2013.01)

(58) Field of Classification Search
    CPC ...................... A61M 5/31511; A61M 5/31515; A61M 2005/3104; A61M 2005/3118; A61M 2005/312
See application file for complete search history.

(56) References Cited

U.S. PATENT DOCUMENTS 5,314,415 A * 5/1994 Liebert et al. ................ 604/218
5,411,488 A     5/1995 Pagay et al.
(Continued)

FOREIGN PATENT DOCUMENTS

CN        1460528 A     12/2003
CN    101085383 A     12/2007
(Continued)

OTHER PUBLICATIONS

Extended Search Report issued on Jul. 7, 2014 by the European Patent Office, in corresponding European Patent Application No. 10849037.6 (6 pages).
(Continued)

*Primary Examiner* — Kami A Bosworth
(74) *Attorney, Agent, or Firm* — Buchanan Ingersoll & Rooney PC

(57) ABSTRACT

A gasket of a prefilled syringe is disclosed, which includes a gasket body and a plunger-mounting member. The gasket body has a plunger-mounting member removal prevention rib formed on an inner surface of the gasket body. The plunger-mounting member has an outer projected part, which engages the plunger-mounting member removal prevention rib of the gasket body, a plurality of elastically deformable inner projected parts which are extended obliquely from an inner portion of a proximal side of the plunger-mounting member toward a central and distal end of the plunger-mounting member, and plunger removal prevention locking parts formed at free ends of the inner projected parts. The plunger has a distal end part capable of entering the plunger-mounting member and an outer projection part which engages the plunger removal prevention locking parts of the plunger-mounting member.

21 Claims, 21 Drawing Sheets

(56) References Cited

U.S. PATENT DOCUMENTS

| | | | |
|---|---|---|---|
| 5,688,252 A * | 11/1997 | Matsuda et al. | 604/218 |
| 5,722,951 A | 3/1998 | Marano | |
| 5,947,935 A * | 9/1999 | Rhinehart et al. | 604/218 |
| 6,432,089 B1 | 8/2002 | Kakimi et al. | |
| 8,342,371 B2 * | 1/2013 | Helmenstein | 222/327 |
| 8,343,094 B2 | 1/2013 | Shaw | |
| 8,475,415 B2 | 7/2013 | Schiller et al. | |
| 8,636,688 B2 | 1/2014 | Shaw | |
| 2005/0182371 A1 * | 8/2005 | Wagner et al. | 604/218 |
| 2006/0069356 A1 * | 3/2006 | Witowski | 604/222 |
| 2007/0260189 A1 | 11/2007 | Shaw et al. | |
| 2008/0132851 A1 | 6/2008 | Shaw et al. | |
| 2008/0300551 A1 | 12/2008 | Schiller et al. | |
| 2011/0034882 A1 | 2/2011 | Quinn et al. | |
| 2012/0136298 A1 | 5/2012 | Bendix et al. | |

FOREIGN PATENT DOCUMENTS

| | | |
|---|---|---|
| CN | 103316404 A | 9/2013 |
| EP | 0692272 A1 | 1/1996 |
| EP | 1166807 A1 | 1/2002 |
| EP | 1 849 490 A1 | 10/2007 |
| JP | 6-39005 U | 5/1994 |
| JP | 9-512727 A | 12/1997 |
| JP | 2004-283466 | 10/2004 |
| JP | 2007-202822 A | 8/2007 |
| JP | 2008-307237 A | 12/2008 |
| JP | 2009-142508 A | 7/2009 |
| WO | WO 2006/087762 A1 | 8/2006 |
| WO | 2007/131086 A2 | 11/2007 |
| WO | 2010139793 A1 | 12/2010 |

OTHER PUBLICATIONS

Office Action issued on Feb. 28, 2014, by the Chinese Patent Office in corresponding Chinese Patent Application No. 201080065717.4. (6 pages).

Notification of Transmittal of Translation of the International Preliminary Report on Patentability (Chapter I or Chapter II)(PCT/IB/338 ), International Preliminary Report on Patentability (Form PCT/IB/373) and the Written Opinion of the International Searching Authority(Translation)(Form PCT/ISA/237) issued on Nov. 1, 2012, in corresponding International Application No. PCT/JP2010/073733. (5 pages).

International Search Report (PCT/ISA/210) issued on Jan. 25, 2011, by Japanese Patent Office as the International Searching Authority for International Application No. PCT/JP2010/073733.

Communication pursuant to Article 94(3) EPC issued Aug. 3, 2016, by the European Patent Office, in corresponding European Patent Application No. 10849037.6. (5 pages).

* cited by examiner

PREFILLED SYRINGE

CROSS REFERENCES TO RELATED APPLICATIONS

This application is a continuation of International Application No. PCT/JP2011/073733 filed on Dec. 28, 2010, and claims priority to Japanese Patent Application JP2010-076389 filed in the Japanese Patent Office on Mar. 29, 2010, the entire content of both of which is incorporated herein by reference.

TECHNICAL FIELD

The present invention relates to a prefilled syringe in which a medicinal solution is filled in advance.

BACKGROUND DISCUSSION

Prefilled syringes are classified into a type in which a plunger is not mounted in advance on a gasket and then mounted on the gasket when the prefilled syringe is used, and a type in which the plunger is mounted on the gasket in advance.

The prefilled syringe in which the plunger is mounted on the gasket in advance can be assembled as follows: after the gasket is inserted into the outer cylinder by using a method called "vacuum capping" in which the gasket is disposed at the opening of the outer cylinder under a pressure-decreased atmosphere (under a vacuum atmosphere) in the state in which a medical agent is filled inside the outer cylinder whose opening disposed at its distal end is sealed, and the plunger is mounted on the gasket at a normal pressure. In a state in which the plunger has been mounted on the gasket, it is relatively difficult to dispose the gasket at the opening of the outer cylinder. Further, it is necessary to additionally take the space in which the pressure is decreased in correspondence to the size of the plunger. Thus, a vacuum capping of a prefilled syringe is performed without mounting the plunger on the gasket. Therefore the prefilled syringe of this type necessitates a plunger-mounting work to be performed subsequently.

In the prefilled syringe of the type in which the plunger is not mounted on the gasket, a user performs an operation of mounting the plunger on the gasket when the user uses the prefilled syringe.

When the plunger is mounted on the gasket by press fit, there is a case in which a pressure generated by the press fit causes the medicinal solution to leak from the gasket or a nozzle of the outer cylinder. Therefore a prefilled syringe in which the gasket and the plunger are coupled to each other by screwing between a female screw formed on the gasket and a male screw formed on the plunger can be used.

There are many cases in which the prefilled syringe is used by mounting it on a syringe pump. The prefilled syringe is set on the syringe pump by mounting a flange disposed at the proximal end portion of the outer cylinder on a holder of the syringe pump and mounting a disk part disposed at the proximal end of the plunger on a fixing groove of a slider of the syringe pump. Some types of syringe pumps have a longitudinal slit for engaging a longitudinal rib with the slider. In such a type of the syringe pump, to fit the rib of the plunger in the longitudinal slit of the slider, it is necessary to make a fine adjustment by rotating the plunger to fit a rib of the plunger in the longitudinal slit of the slider. In the above-disclosed type in which the plunger is mounted on the gasket by using screws, there is a case in which the engagement between the plunger and the gasket is loosened by the plunger-rotating operation.

The prefilled syringe disclosed in European Application Publication No. 1 849 490, International Application Publication WO 2006/087762, has a gasket which slidably obstructs the inside of the barrel where the lure taper part is formed and has the hollow part at the inner circumferential side thereof and the plunger rod. The plunger rod is coupled to the gasket through the anchor part. The anchor part projects from the pedestal part of the tapered surface, which is inclined at the angle of 5 to 45 degrees with respect to the surface of the plunger rod orthogonal to the axial direction thereof and has the distal end contact part, which contacts the back side of the distal end of the gasket and the contact member which is freely fitted on the outer circumferential of the gasket and contacts the inner circumferential wall thereof. The pedestal part has the concave curved surface between the distal-end contact part and the tapered surface. The contact member has the convex curved surface at the portion opposed to the concave curved surface. The barrel has the locking cylinder having the spiral line formed on the inner surface thereof.

The prefilled syringe disclosed in Japanese Patent Application Laid-Open No. 2008-307237 is filled with a medicinal solution and the gasket is inserted into the outer cylinder by the capping work. The prefilled syringe includes the coupler which screws on the proximal end of the gasket, the bottom rod coupled to the coupler at its proximal end, the stopper formed on the coupler, and the engaging part, formed on the bottom rod, which engages the stopper owing to the rotation of the bottom rod in the screwing direction. When the stopper contacts the engaging part in the direction opposite to the screwing direction, the stopper elastically deforms and does not engage the engaging part.

As disclosed in Japanese Patent Application Laid-Open No. 2009-142508, the syringe has the gasket, the outer cylinder, and the plunger. The plunger has the spiral rib formed on the outer surface of the head part. The gasket has the spiral screwing part which screws on the spiral rib, the annular rib, to help prevent the separation of the plunger from the gasket, which is located at a position in the vicinity of the spiral screwing part and distal therefrom, and the accommodation part for accommodating the portion where the spiral rib of the head part of the plunger is formed. The annular rib has the rib-absent portion for guiding the spiral rib which has reached the annular rib owing to the progress of the screwing between the spiral rib of the plunger and the spiral screwing part of the gasket to the accommodation part.

In the prefilled syringes disclosed in Japanese Patent Application Laid-Open No. 2008-307237 and Japanese Patent Application Laid-Open No. 2009-142508, it is necessary to perform a work of rotating the plunger to mount the plunger on the gasket. In the prefilled syringe disclosed in Japanese Patent Application Laid-Open No. 2008-307237, it is not necessary to rotate the plunger to mount the plunger on the gasket, nor to mount the plunger on the gasket by pressing the distal end portion of the plunger into the gasket. But during the work of mounting the plunger on the gasket, there is a relatively high possibility that the distal end portion of the plunger deforms the gasket, thus causing a medicinal solution to leak. In addition, there is a possibility that after the plunger is mounted on the gasket, the distal end portion of the plunger deforms the gasket when the plunger is pressed, thus causing the medicinal solution to leak.

SUMMARY

According to an aspect, a prefilled syringe includes a plunger, which is mountable on a gasket by pressing the plunger into the gasket without applying relatively high pressure to the gasket. The mounting of the plunger and the gasket as disclosed helps prevent the gasket from becoming loose when the plunger is rotated.

According to another aspect, a prefilled syringe includes a prefilled syringe body having an outer cylinder, a gasket slidably accommodated inside the outer cylinder, and a sealing member, which seals an opening formed at a distal end of the outer cylinder. A medical agent is accommodated inside a medical agent accommodation part formed inside the outer cylinder. A plunger is mounted or mountable on the gasket. The gasket is composed of a gasket body having a tubular body with a closed distal end and an open proximal end. The gasket body also has an inner cavity extended from an opening formed at the proximal end of the gasket to the distal end of the gasket. A plunger-mounting member is mounted on the gasket body. The gasket body includes a plunger-mounting member removal prevention rib formed on an inner surface of the inner cavity. The plunger-mounting member is formed as a tubular body which has a hollow portion penetrating therethrough from a distal end of the plunger-mounting member to a proximal end of the plunger-mounting member and can be accommodated inside the inner cavity of the gasket body. The plunger-mounting member also includes an outer projected part formed on an outer surface of the plunger-mounting member, which engages a plunger-mounting member removal prevention rib of the gasket body, which helps prevent the plunger-mounting member from separating from the gasket body. A plurality of elastically deformable inner projected parts extended obliquely from an inner portion of a proximal side of the plunger-mounting member toward a central and distal end of the plunger-mounting member and has a free end respectively at a position which does not reach a center of the plunger mounting member. Plunger removal prevention locking parts are formed at the free ends of the inner projected parts respectively. The plunger has a pressing part capable of pressing a proximal end portion of the gasket body in an operation of mounting the plunger on the gasket. A distal end part projects from the pressing part toward the distal end of the plunger and is capable of entering the plunger-mounting member. An outer projection part is disposed on an outer surface of the distal end part and engages the plunger removal prevention locking parts of the plunger-mounting member. The plunger-mounting member is mounted on the gasket body in a state in which the plunger-mounting member removal prevention rib of the gasket body and the outer projected part of the plunger-mounting member have engaged each other. When the plunger is mounted on the gasket, the distal end part of the plunger does not contact an inner surface of the gasket body.

By way of example, by pressing the distal end portion of the plunger into the plunger-mounting member, the plunger is mounted on the body of the prefilled syringe and it is unnecessary to rotate the plunger in the operation of mounting the plunger on the body of the prefilled syringe. In addition it is possible to help restrain the gasket from being removed from the plunger mounted on the body of the prefilled syringe. Although the plunger mounted on the body of the prefilled syringe is rotated, the rotational force of the plunger is not transmitted to the gasket body, which helps prevent the gasket from becoming deformed and causing leaking of liquid from the gasket.

Another aspect involves a gasket and plunger assembly for a prefilled syringe which includes a gasket body, with the gasket body having a plunger-mounting member removal prevention rib formed on an inner surface of the gasket body. The plunger-mounting member has an outer projected part which engages the plunger-mounting member removal prevention rib of the gasket body. A plurality of elastically deformable inner projected parts extend obliquely from an inner portion of a proximal side of the plunger-mounting member toward a central and distal end of the plunger-mounting member, and plunger removal prevention locking parts are formed at free ends of the inner projected parts. The assembly also includes a plunger having a distal end part configured to enter the plunger-mounting member and an outer projection part which engages the plunger removal prevention locking parts of the plunger-mounting member.

A further aspect involves a syringe which includes a syringe body having an outer cylinder, a gasket slidably accommodated inside the outer cylinder, and a sealing member which seals an opening formed at a distal end of the outer cylinder, and a plunger mountable on the gasket. A medical agent accommodation part is formed inside the outer cylinder. The gasket is composed of a gasket body having a tubular body with a closed distal end and an open proximal end. The gasket has an inner cavity extending from an opening formed at the proximal end of gasket body to the distal end of the gasket body and a plunger-mounting member mounted on the gasket body. The gasket body has a plunger-mounting member removal prevention rib formed on an inner surface of the inner cavity. The plunger-mounting member is formed as a tubular body which has a hollow portion penetrating therethrough from a distal end of the tubular body to a proximal end of the tubular body, and configured to be accommodated inside the inner cavity of the gasket body. The plunger-mounting member has an outer projected part formed on an outer surface of the plunger-mounting member and configured to engage a plunger-mounting member removal prevention rib of the gasket body, and a plurality of elastically deformable inner projected parts which are extended obliquely from an inner portion of a proximal side of the plunger-mounting member toward a central and distal end of the plunger-mounting member and having a free end at a position which does not reach a center of the plunger-mounting member. Plunger removal prevention locking parts are formed at the free ends of the inner projected parts. The plunger having a pressing part configured of pressing a proximal end portion of the gasket body in an operation of mounting the plunger on the gasket, a distal end part projecting from the pressing part toward the distal end thereof and configured to enter the plunger-mounting member, and an outer projection part disposed on an outer surface of the distal end part and engaging the plunger removal prevention locking parts of the plunger-mounting member. The plunger-mounting member is mounted on the gasket body in a state in which the plunger-mounting member removal prevention rib of the gasket body and the outer projected part of the plunger-mounting member have engaged each other. When the plunger is mounted on the gasket, the distal end part of the plunger does not contact an inner surface of the gasket body.

DETAILED DESCRIPTION

Figure 1:
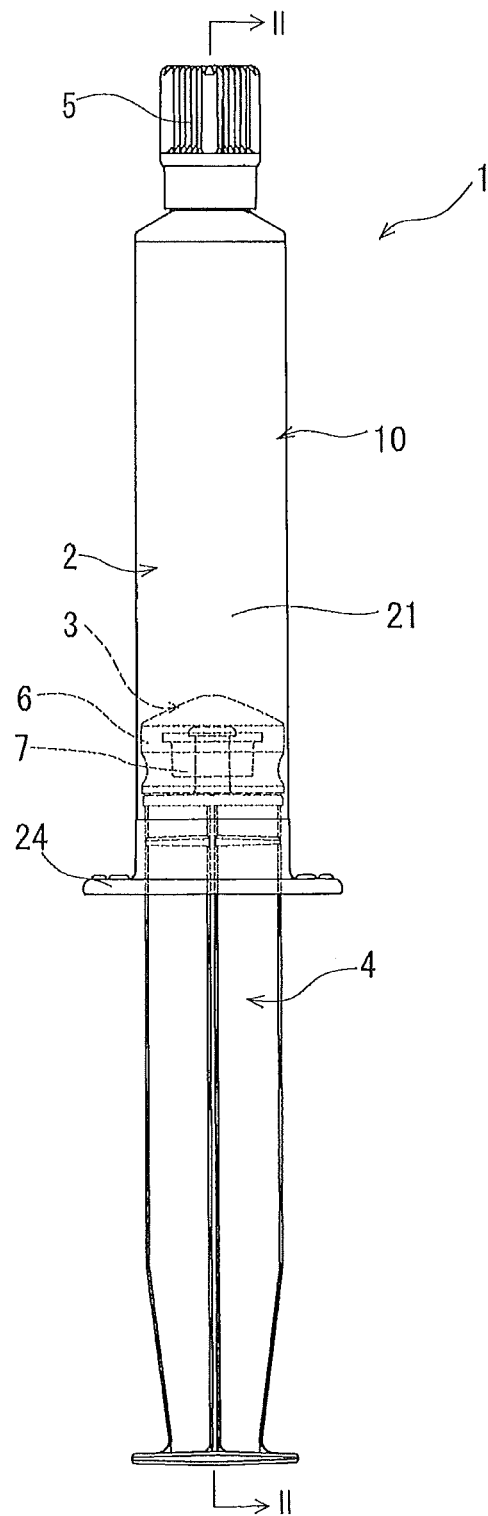
FIG. 1 is a front view of a prefilled syringe of an embodiment of the present disclosure.

The prefilled syringe of the present disclosure is disclosed below by using embodiments shown in the drawings.

A prefilled syringe 1 of the present disclosure has a prefilled syringe body 10 including an outer cylinder 2, a gasket 3 slidably accommodated inside the outer cylinder 2, a sealing member 5 which seals an opening formed at a distal end of the outer cylinder 2, and a medical agent 8 accommodated inside a medical agent accommodation part formed inside the outer cylinder 2; and a plunger 4 which is mounted on the gasket 3 or mountable thereon.

The gasket 3 is a tubular body having a closed distal end and an open proximal end and composed of a gasket body 6 which has an inner cavity 60 extended from an opening formed at the proximal end thereof to the distal end thereof and a plunger-mounting member 7 mounted on the gasket body 6. The gasket body 6 has a plunger-mounting member removal prevention rib 62 formed on an inner surface of the inner cavity 60. The plunger-mounting member 7 is a tubular body having a hollow portion penetrating therethrough from a distal end thereof to a proximal end thereof and can be accommodated inside the inner cavity 60 of the gasket body 6. The plunger-mounting member 7 has an outer projected part 73 which is formed on an outer surface thereof and engages the plunger-mounting member removal prevention rib 62 of the gasket body 6, and helps prevent the plunger-mounting member 7 from separating from the gasket body 6, a plurality of elastically deformable inner projected parts 75a, 75b, 75c, 75d, 75e, and 75f which are extended obliquely from an inner portion of a proximal side of the plunger-mounting member 7 toward a central and distal end thereof and have a free end respectively at a position which does not reach the center of the plunger-mounting member, and a plurality of plunger removal prevention locking parts 76a, 76b, 76c, 76d, 76e, and 76f formed at the free ends of the inner projected parts 75a, 75b, 75c, 75d, 75e, and 75f, respectively. The plunger 4 has a pressing part 45 capable of pressing a proximal end portion 67 of the gasket body 6 in an operation of mounting the plunger 4 on the gasket 3, a distal end part 42 (in this embodiment, tubular distal end part) which is projected from the pressing part 45 toward the distal end of the plunger 4 and capable of entering the plunger-mounting member 7, and an outer projection part 43 which is disposed on the outer surface of the tubular distal end part 42 and engages the plunger removal prevention locking parts 76a, 76b, 76c, 76d, 76e, and 76f of the plunger-mounting member 7. A plurality of ribs 68 is formed on the proximal end surface (rear end portion) of the gasket body 6 of this embodiment.

The plunger-mounting member 7 is mounted on the gasket body 6 in a state in which the plunger-mounting member removal prevention rib 62 of the gasket body 6 and the outer projected part 73 of the plunger-mounting member 7 have engaged each other. When the plunger 4 is mounted on the gasket 3, the distal end of the tubular distal end part 42 of the plunger 4 does not contact the inner surface of the gasket body 6.

The prefilled syringe 1 of this embodiment is composed of the prefilled syringe body 10 and the plunger 4 mounted on the prefilled syringe body 10 (gasket 3).

The prefilled syringe body 10 has the outer cylinder 2, the sealing member 5 which seals the opening formed at the distal end of the outer cylinder 2, the gasket 3 slidably accommodated inside the outer cylinder 2, and the medical agent 8 accommodated inside the medical agent accommodation part formed inside the outer cylinder 2.

The gasket 3 is composed of the gasket body 6 and the plunger-mounting member 7 mounted thereon.

As shown in FIGS. 1 through 7, the gasket body 6 is the tubular body having the closed distal end and the inner cavity 60 extended from the opening formed at the proximal end of the gasket body 6 toward the distal end thereof. The gasket body 6 has a tapered part 61, the diameter of which taperingly decreases toward the distal end thereof. The gasket body 6 has a distal side annular rib 63 formed at the distal side of the outer surface thereof and a proximal side annular rib 64 formed at the proximal side of the outer surface thereof.

The gasket body 6 has the inner cavity 60 which is an accommodation part accommodating the plunger-mounting member. The inner cavity 60 has the plunger-mounting member removal prevention rib 62 formed on the inner surface thereof. In this embodiment, the plunger-mounting member removal prevention rib 62 is disposed at the distal side of the inner cavity 60. The plunger-mounting member removal prevention rib 62 is formed as an endless annular rib almost orthogonal to the axis of the gasket body 6. By way of example, the plunger-mounting member removal prevention rib 62 is formed as the annular rib, plunger-mounting member removal prevention rib 62 may be formed as a plurality of uncontinuous ribs disposed on the same circumference. A distal end surface of the plunger-mounting member removal prevention rib 62 is formed as an annular erect surface 62a erect from the inner surface of the inner cavity 60. A proximal end surface of the plunger-mounting member removal prevention rib 62 is formed as an annular inclined surface 62b the diameter of which increases toward the proximal end thereof. According to an aspect, the plunger-mounting member removal prevention rib 62 has an equal inner diameter portion which has a substantially equal inner diameter and is extended in a predetermined length. By providing the plunger-mounting member removal prevention rib 62 with the equal inner diameter portion, it is possible to help prevent the plunger-mounting member from separating from the gasket body when the plunger is pulled rearward. The height of the plunger-mounting member removal prevention rib 62 can be about 0.5 to 2.0 mm, for example, about 1.0 to 1.5 mm. The length of the equal inner diameter portion of the plunger-mounting member removal prevention rib 62 can be 1.0 to 6.0 mm, for example, about 2.0 to 4.0 mm.

The gasket body 6 has a projection part 66 projected from the central portion of the inner surface of the distal end portion thereof toward the proximal side thereof. The projection part 66 is capable of contacting the distal end of the tubular distal end part 42 of the plunger 4, when the distal end portion of the gasket body 6 deforms toward its proximal side, which helps prevent the distal end portion of the gasket body 6 from excessively deforming. According to one aspect, the projection part 66 is approximately semi-spherical. Generally the diameter of the gasket body 6 is about 5 to 30 mm, and the whole length thereof is about 5 to 30 mm.

As constituent materials of the gasket body 6, known materials conventionally used for the gasket can be used. For example, rubber, elastomer, polyolefin resin, fluororesin, and polyester resin are listed. As the rubber, natural rubber, isoprene rubber, butyl rubber, chloroprene rubber, nitrile-butadiene rubber, styrene butadiene rubber, and silicone rubber are favorable. By way of example, the above-disclosed rubbers are vulcanized. As the elastomer, by way of example, polyvinyl chloride elastomer, polyolefin elastomer, styrene elastomer, polyester elastomer, polyamide elastomer, polyurethane elastomer, and mixtures of these elastomers are used. Of the above-disclosed rubbers and elastomers, the styrene butadiene rubber, the butyl rubber, and the styrene elastomer can be used because these materials have suitable hardness and elastic properties and various sterilization methods such as γ ray sterilization, electron beam sterilization, and high-pressure steam sterilization can be adopted therefor.

For example, the distal end of the gasket body 6 may be coated with a medical agent low absorption substance.

As materials of a medical agent low absorption layer, known materials which are conventionally used for a laminate gasket can be used. As the materials of the low-degree medical agent absorption layer, polyolefin resin, fluororesin, polyester resin, and poly-para-xylylene are listed. For example, as the polyolefin resin, polypropylene, ultra-high-molecular-weight polyethylene, poly (4-methylpentene-1), and cyclic polyolefin can be used. By way of example, the fluororesin, a tetrafluoroethylene-perfluoroethoxyethylene copolymer, polytetrafluoroethylene, a tetrafluoroethylene/ perfluoroalkyl vinyl ether copolymer, a tetrafluoroethylene/ hexafluoropropylene copolymer can be used.

A lubricant can be applied to the outer surface of the gasket body 6 and to at least the surface of the distal side annular rib 63 and that of the proximal side annular rib 64. The lubricant may be applied to the inner surface of the outer cylinder. As the lubricant, for example, silicone oil can be used.

By forming a silicone resin layer on the surface of the gasket body by solidifying the silicone resin, this helps eliminate the need for the use of the lubricant such as the silicone oil.

As shown in FIGS. 2, 4, 8 through 12, the plunger-mounting member 7 is a tubular body which has the hollow portion penetrating therethrough from a distal end thereof to a proximal end thereof. The plunger-mounting member 7 has a body part 71 which can be accommodated inside the inner cavity 60 of the gasket body 6, the outer projected part 73 formed on the outer surface of the body part 71, a plurality of the elastically deformable inner projected parts 75a, 75b, 75c, 75d, 75e, and 75f, and the plunger removal prevention locking parts 76a, 76b, 76c, 76d, 76e, and 76f formed at the free ends of the inner projected parts 75a, 75b, 75c, 75d, 75e, and 75f respectively.

The outer projected part 73 engages the plunger-mounting member removal prevention rib 62 of the gasket body 6, which helps prevent the plunger-mounting member 7 from separating from the gasket body 6. In the plunger-mounting member 7 of this embodiment, the outer projected part 73 is formed on the outer surface of the distal end portion (specifically, the outer surface of the distal end) of the body part 71 as the annular projected part almost orthogonal to the axis of the plunger-mounting member 7. The proximal end surface of the outer projected part (outer annular projected part) 73 is formed as an annular erect surface 73a erect from the outer surface of the body part 71. The outer projected part 73 is not limited to an annular configuration, but may be constructed of a plurality of uncontinuous projected parts. By way of example, the height of the outer projected part 73 can be 0.5 to 2.0 mm, for example, 1.0 to 1.5 mm. The outer diameter of the outer projected part 73 of the plunger-mounting member 7 is larger than the inner diameter of the plunger-mounting member removal prevention rib 62 of the gasket body 62 by 1.0 to 4.0 mm and for example, by 2.0 to 3.0 mm.

As shown in FIGS. 4, 9 through 12, the plunger-mounting member 7 has a plurality of the elastically deformable inner projected parts 75a, 75b, 75c, 75d, 75e, and 75f which are extended obliquely from the inner portion of a proximal end 72 of the plunger-mounting member 7 (body part 71) toward the central and distal end thereof and have the free end at the position respectively which does not reach the center of the plunger-mounting member 7. There are formed the plunger removal prevention locking parts 76a, 76b, 76c, 76d, 76e, and 76f at the free ends of the inner projected parts 75a, 75b, 75c, 75d, 75e, and 75f respectively. The plunger removal prevention locking parts 76a, 76b, 76c, 76d, 76e, and 76f are engageable with the outer projection part 43 formed on the outer surface of the tubular distal end part 42 of the plunger 4 to be disclosed later. The body part 71 is a cylindrical part having an almost equal outer diameter and extending in a predetermined length and accommodates the tubular distal end part 42 of the plunger 4 to be disclosed later.

In the plunger-mounting member 7 of this embodiment, each of the inner projected parts 75a, 75b, 75c, 75d, 75e, and 75f is extended obliquely at a predetermined angle from the inner portion of the proximal end 72 of the plunger-mounting member 7 (body part 71) toward the central and distal end thereof. Each of the inner projected parts 75a, 75b, 75c, 75d, 75e, and 75f has the free end at the position which does not reach the center of the plunger-mounting member and becomes smaller toward the free end in the width thereof. In this embodiment, each of the inner projected parts 75a, 75b, 75c, 75d, 75e, and 75f becomes gradually smaller toward the free end in the width thereof.

In the plunger-mounting member 7 of this embodiment, the plunger removal prevention locking parts 76a, 76b, 76c, 76d, 76e, and 76f are formed on the distal end surfaces of the free ends of the inner projected parts 75a, 75b, 75c, 75d, 75e, and 75f of the plunger-mounting member respectively. The plunger removal prevention locking parts (distal end surfaces of the free ends) 76a, 76b, 76c, 76d, 76e, and 76f are formed as flat surfaces almost orthogonal to the axis of the plunger-mounting member 7. "Almost orthogonal" as disclosed herein means a concept including inclinations less than ±20 degrees with respect to "orthogonal" (90 degrees). In this embodiment, the plunger removal prevention locking parts 76a, 76b, 76c, 76d, 76e, and 76f incline about 10 degrees with respect to "orthogonal" (90 degrees).

In accordance with an aspect, the number of the inner projected parts is not less than two inner projected parts almost equiangularly with respect to the axis of the plunger-mounting member 7. For example, the number of the inner projected parts is four to eight.

Each of the inner projected parts of the plunger-mounting member is elastically deformable. When the inner projected parts are pressed toward the proximal end thereof, the free ends of the inner projected parts deform in a direction in which the free ends become close to the center of the plunger-mounting member. When the inner projected parts are pressed toward the distal end thereof, the free ends deform in a direction in which the free ends become distant from the center of the plunger-mounting member.

In the plunger-mounting member 7 of this embodiment, the proximal end surfaces of the inner projected parts 75a, 75b, 75c, 75d, 75e, and 75f of the plunger-mounting member 7 are formed as flat and smooth inclined surfaces inclined toward the center of the plunger-mounting member to form a guide portion for guiding the engagement between the outer projection part of the plunger 4 and the locking parts of the plunger-mounting member. For example, the inner surfaces of the free ends of the inner projected parts 75a, 75b, 75c, 75d, 75e, and 75f of the plunger-mounting member 7 form a circular-arc surface whose center almost aligns with the axis of the plunger-mounting member 7.

Figure 4:
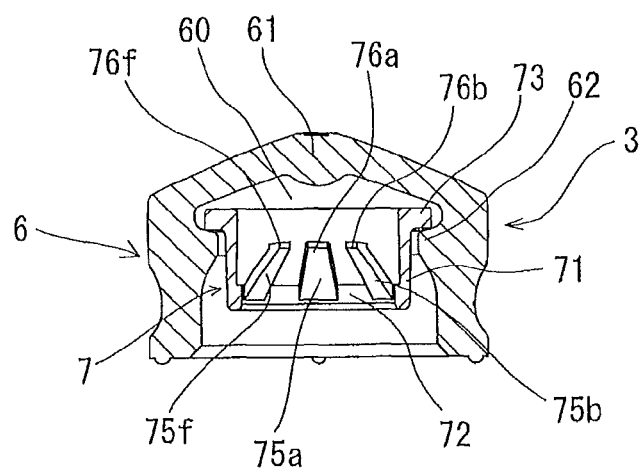
FIG. 4 is a cross-sectional view of the gasket taken along the section line IV-IV in FIG. 3.
Figure 5:
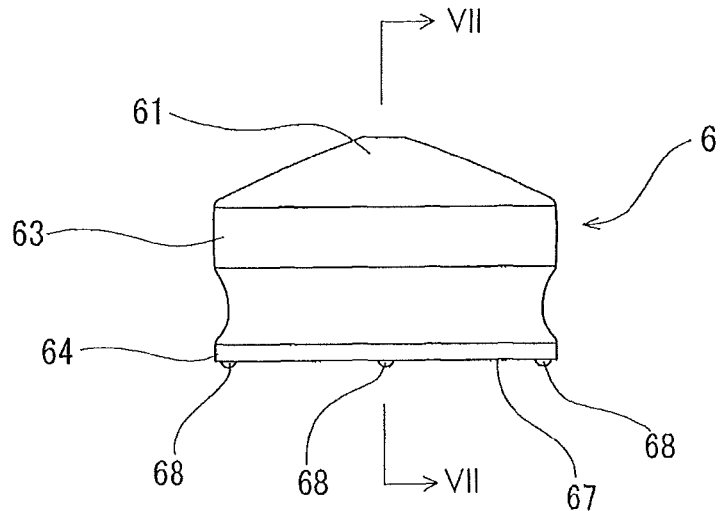
FIG. 5 is a front view of a gasket body for use in the gasket shown in FIG. 3.
Figure 6:
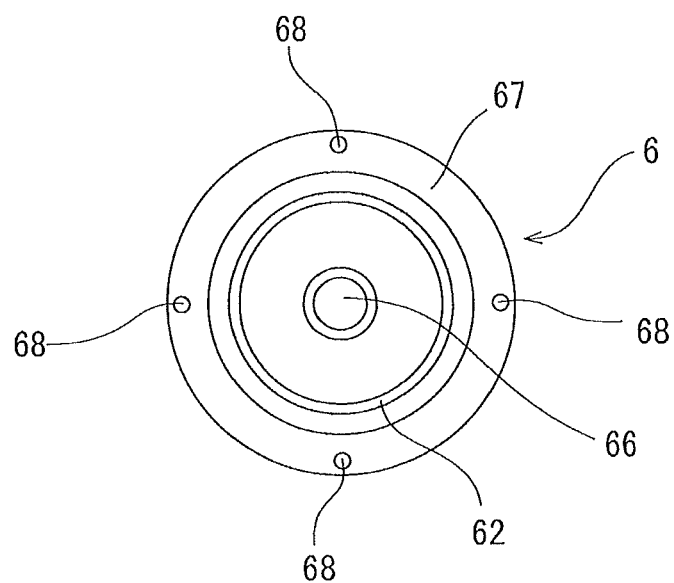
FIG. 6 is a bottom view of the gasket body shown in FIG. 5.
Figure 7:
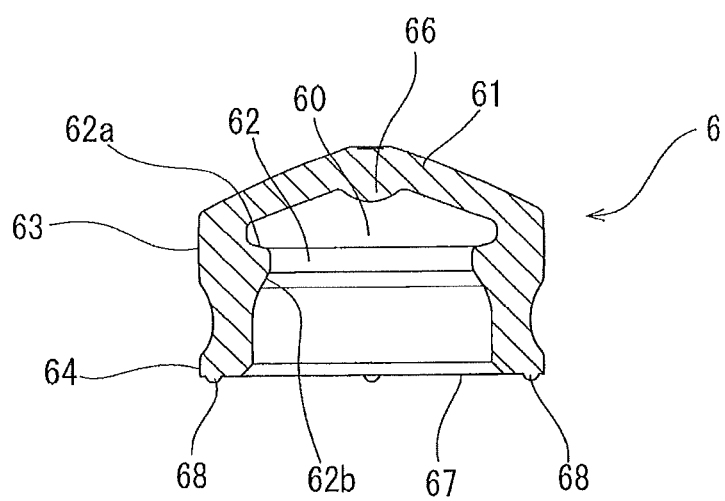
FIG. 7 is a cross-sectional view of the gasket body taken along the section line VII-VII in FIG. 5.
Figure 8:
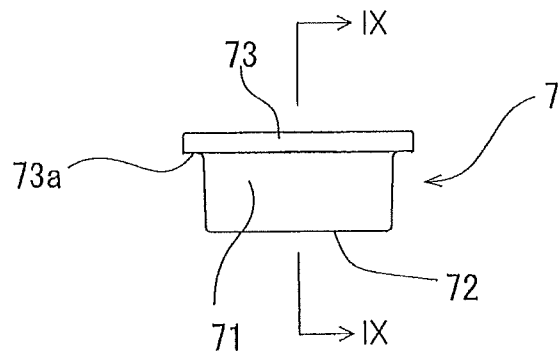
FIG. 8 is a front view of a gasket-mounting member for use in the gasket shown in FIG. 3.
Figure 9:
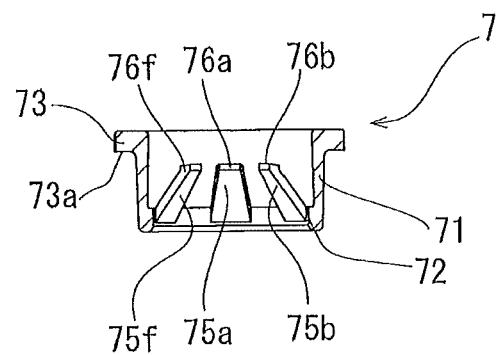
FIG. 9 is a cross-sectional view taken along the section line IX-IX in FIG. 8.
Figure 10:
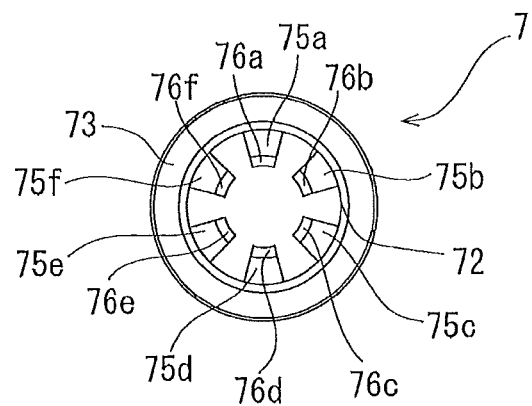
FIG. 10 is a plan view of the gasket-mounting member shown in FIG. 8.
Figure 11:
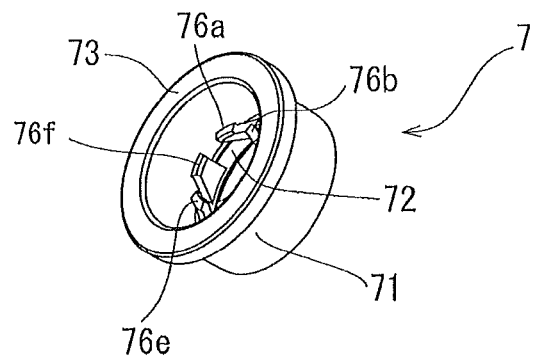
FIG. 11 is a perspective view of the gasket-mounting member shown in FIG. 8 as viewed from a distal side of gasket-mounting member.
Figure 12:
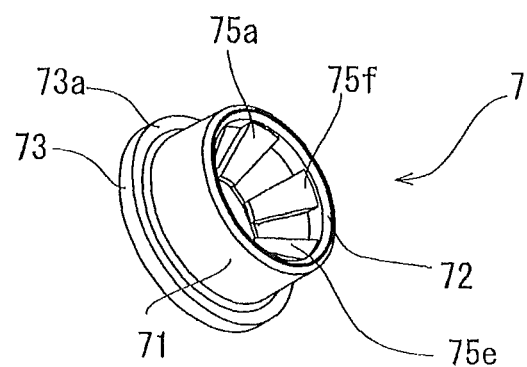
FIG. 12 is a perspective view of the gasket-mounting member shown in FIG. 8 as viewed from a proximal side of gasket-mounting member.

As shown in FIG. 4, the plunger-mounting member 7 is mounted on the gasket body 6 in the state in which the plunger-mounting member removal prevention rib 62 of the gasket body 6 and the outer projected part 73 of the plunger-mounting member 7 have engaged each other. The proximal end of the plunger-mounting member 7 mounted on the gasket body 6 does not project beyond the gasket body 6. For example, in a state in which the plunger-mounting member 7 has been mounted on the gasket body 6, the proximal end of the plunger-mounting member 7 is located at a position distal from the proximal end of the gasket body by a predetermined length. In the state in which the plunger-mounting member 7 has been mounted on the gasket body 6, the body part 71 of the plunger-mounting member 7 is not pressed against the plunger-mounting member removal prevention rib 62 nor the outer projected part 73 of the plunger-mounting member 7 is pressed against the inner surface of the inner cavity 60 of the gasket body 61.

Therefore when the plunger-mounting member is mounted on the gasket body 6, the plunger-mounting member 7 is rotatable and a little longitudinally movable inside the gasket body 6. For example, the outer diameter of the plunger-mounting member 7 of the body part 71 is larger than the inner diameter of the plunger-mounting member removal prevention rib 62 of the gasket body 6 by 1.0 to 4.0 mm and the outer diameter of the outer projected part 73 is larger than the inner diameter of the plunger-mounting member removal prevention rib 62 by way of example, 2.0 to 3.0 mm.

By way of example, a hard or semi-hard resin such as high-density polyethylene, polypropylene, polystyrene, and polyethylene terephthalate can be used for materials composing the plunger-mounting member 7.

As shown in FIGS. 1, 2, 13 through 15, the plunger 4 has a plunger body part 41, the pressing part 45 capable of pressing the proximal end surface of the gasket 3 when the plunger 4 is mounted on the gasket 3, the tubular distal end part 42 projected from the pressing part 45 toward the distal end of the plunger 4 and is capable of penetrating into the hollow portion of the plunger-mounting member 7, and the outer projection part 43 which is disposed on the outer surface of the tubular distal end part 42 and engages the plunger removal prevention locking parts 76a, 76b, 76c, 76d, 76e, and 76f of the plunger-mounting member 7. For example, although the distal end part 42 is tubular, the configuration thereof is not limited to the tubular configuration, but may be solid.

The plunger 4 can be mounted on the plunger-mounting member 7 by pressing the distal end part 42 into the hollow portion of the plunger-mounting member 7. In the state in which the plunger 4 is mounted on the gasket 3, the distal end part 42 of the plunger 4 does not contact the inner surface of the gasket body 6.

Figure 13:
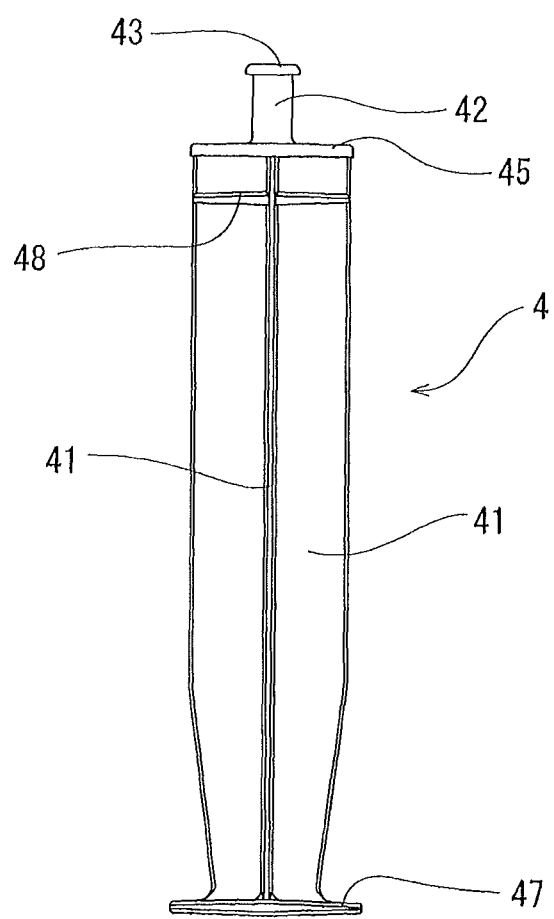
FIG. 13 is an enlarged front view of a plunger for use in the prefilled syringe of the present disclosure.
Figure 14:
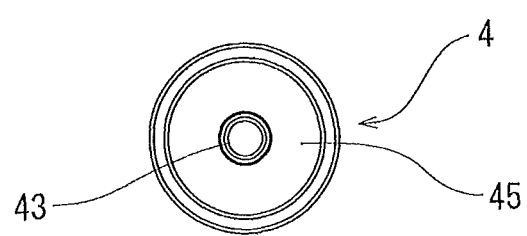
FIG. 14 is a plan view of the plunger shown in FIG. 13.
Figure 15:
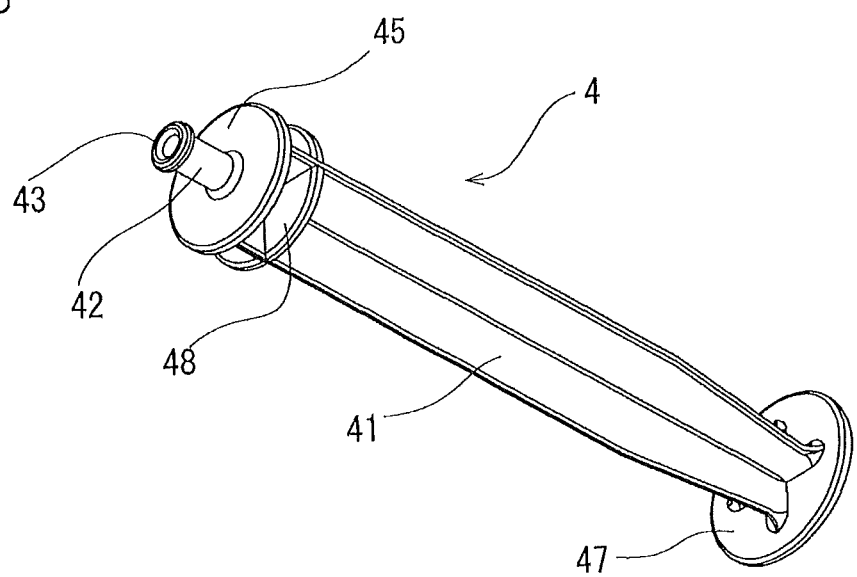
FIG. 15 is a perspective view of the plunger shown in FIG. 13.

The pressing part 45 is positioned at the distal end of the plunger body part 41 and formed in the shape of a disk. As shown in FIGS. 13 and 15, the plunger body part 41 is formed in the shape of a cross. The pressing part 45 is disposed at the distal end of the plunger body part 41. A disk-shaped proximal end pressing part 47 is formed at the proximal end of the body part 41. The plunger 4 has a reinforcing rib 48 disposed midway between the pressing part 45 and the proximal end pressing part 47.

By way of example, at to materials composing the plunger 4, a hard resin or a semi-hard resin such as the high-density polyethylene, the polypropylene, polystyrene, and the polyethylene terephthalate can be used.

In the plunger 4 of this embodiment, the outer projection part 43 which engages the plunger removal prevention locking parts 76a, 76b, 76c, 76d, 76e, and 76f of the plunger-mounting member 7 is formed on the outer surface of the distal end portion (specifically, outer surface of distal end) of the tubular distal end part 42 as the annular outer projection part almost orthogonal to the axis of the tubular distal end part 42 of the plunger 4. The proximal end surface of the outer projection part (outer annular projection part) 43 is formed as an annular erect surface erect from the outer surface of the tubular distal end part 42. The tubular distal end part 42 is not necessarily limited to the annular configuration, but may consist of a plurality of uncontinuous projections. The height of the outer projection part 43 can be about 0.3 to 1.5 mm, for example, about 0.5 to 1.0 mm. The outer diameter of the plunger 4 at the outer projection part 43 thereof is larger than the diameter of the circle formed of the inner surfaces of the free ends of the inner projected parts 75a, 75b, 75c, 75d, 75e, and 75f of the plunger-mounting member 7 by 0.5 to 3.0 mm, for example, by 1.0 to 2.0 mm.

By pressing the tubular distal end part 42 of the plunger 4 including the outer projection part 43 into the hollow portion of the plunger-mounting member 7, the outer projection part 43 presses and elastically deforms the inner projected parts 75a, 75b, 75c, 75d, 75e, and 75f of the plunger-mounting member 7 and passes through inner projected parts 75a, 75b, 75c, 75d, 75e, and 75f. Thereafter the inner projected parts 75a, 75b, 75c, 75d, 75e, and 75f are restored to the original configuration thereof or to an almost original configuration thereof. Thereby the proximal end surface of the outer projection part 43 engages the plunger removal prevention locking parts 76a, 76b, 76c, 76d, 76e, and 76f, which helps prevent the plunger 4 from separating from the plunger-mounting member 7.

Figure 16:
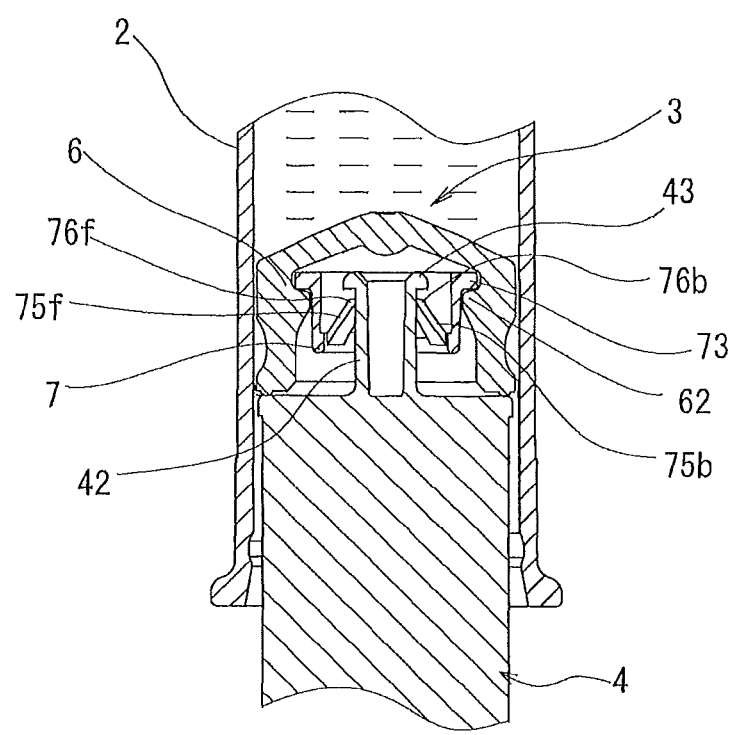
FIG. 16 is an explanatory view for explaining an operation of mounting the plunger on the body of the prefilled syringe.

In the plunger 4 of this embodiment, in a state in which the plunger 4 has been mounted on the plunger-mounting member 7, the inner surface of the free end of each of the inner projected parts 75a, 75b, 75c, 75d, 75e, and 75f is in contact with the outer surface of the tubular distal end part 42 of the plunger 4. As shown in FIG. 16, in the state in which the plunger 4 has been mounted on the plunger-mounting member 7, the inner surface of the free end of each of the inner projected parts 75a, 75b, 75c, 75d, 75e, and 75f may contact the outer surface of the tubular distal end part 42 of the plunger 4 under pressure with the inner surface of the free end of each of the inner projected parts 75a, 75b, 75c, 75d, 75e, and 75f being pressed a little in a direction in which the free ends thereof are expanded a little, which helps prevent the gasket from loosening.

Figure 2:
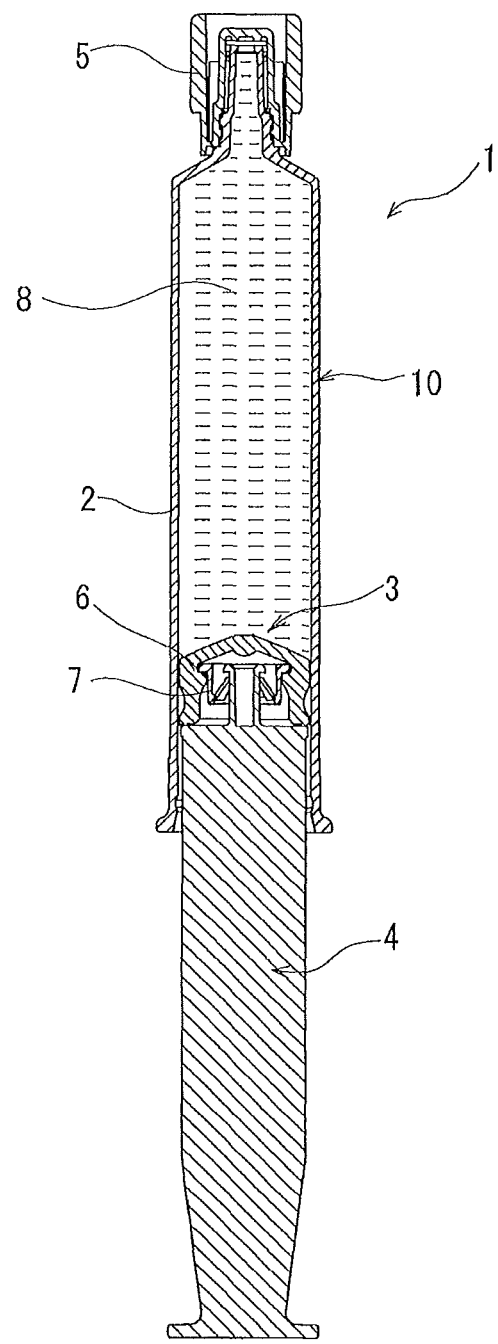
FIG. 2 is a cross-sectional view of the syringe taken along the section line II-II in FIG. 1.
Figure 3:
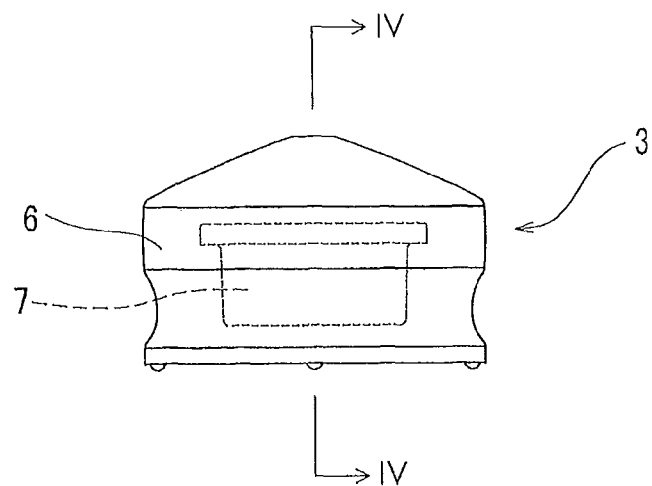
FIG. 3 is an enlarged front view of a gasket for use in the prefilled syringe of the present disclosure.

As shown in FIGS. 1, 2, and 16, in the prefilled syringe of this embodiment, the gasket 3 is disposed at a position distal from the proximal end of the outer cylinder in a predetermined length, and the pressing part 45 of the plunger 4 mounted on the plunger-mounting member 7 is positioned inside the outer cylinder, which helps prevent the gasket mounted in the outer cylinder from inclining.

The outer cylinder 2 has an outer cylinder body part 21, a nozzle part 22 disposed at the distal end portion of the outer cylinder body part 21, and a flange 24 disposed at the proximal end portion of the outer cylinder body part 21.

The body part 21 of the outer cylinder is an almost tubular part accommodating the gasket 3 liquid-tightly and slidably. The nozzle part 22 is a tubular part having a smaller diameter than the outer cylinder body part 21 of the outer cylinder. The distal end portion (shoulder part) of the outer cylinder body part 21 becomes taperingly smaller toward the nozzle part 22.

By way of example, the outer cylinder 2 is a tubular body formed of a transparent or semitransparent material and formed of a low oxygen-permeable and vapor-permeable material.

Figure 17:
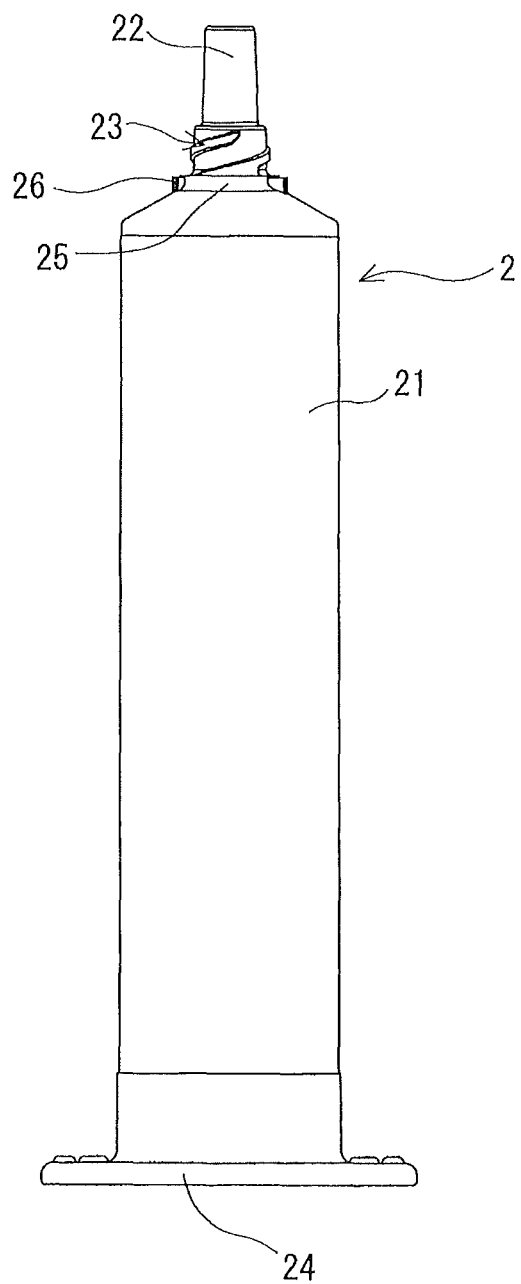
FIG. 17 is a front view of an outer cylinder for use in the prefilled syringe of the present disclosure.

As shown in FIGS. 1 and 17, the flange 24 is an elliptic donut-shaped disk part projected vertically from the entire circumference of the proximal end of the outer cylinder body part 21. The flange 24 has two wide gripping portions opposed to each other. A plurality of ribs is formed on the distal end surface of each gripping portion. The proximal end surface of the flange 24 is formed as a concave part except the peripheral portion of the flange 24 and a portion of the flange 24 formed on the proximal end portion of the outer cylinder as rib portions.

As shown in FIG. 17, the nozzle part 22 has a needle-mounting portion, the diameter of which decreases toward its distal end. In this embodiment, a nozzle-side screwing portion 23 is formed at a position proximal from a tip portion. Although the sealing member 5 is mounted on the outer cylinder by means of the nozzle-side screwing portion 23 in this embodiment, the sealing member 5 may be mounted thereon by other means.

As shown in FIG. 17, in this embodiment, the nozzle part 22 has a base portion 25 disposed between the proximal end of the tip and the body part 21 of the outer cylinder. The nozzle part 22 has a nozzle-side engaging portion 26 formed on the side surface of the base portion 25. The nozzle-side engaging portion 26 is formed of a rib.

As materials forming the outer cylinder 2, various resins such as polypropylene, polyethylene, polystyrene, polyamide, polycarbonate, polyvinyl chloride, poly-(4-methylpentene-1), acrylic resin, acrylonitrile-butadiene-styrene copolymer, polyester such as polyethylene terephthalate, and cyclic polyolefin are listed. Of these resins, resins such as the polypropylene and the cyclic polyolefin, for example, can be easily molded and are heat-resistant. As the materials forming the outer cylinder 2, to help enhance the sealing performance, for example, resins having a higher hardness than the material of the sealing member can be used. Thereby, in an operation of mounting the sealing member 5 on the nozzle part 22, the sealing member 5 adheres to the nozzle part 22 by performing a screwing operation and thus the sealing performance can be further enhanced.

By way of example, as to the medicinal solution 8 to be filled inside the syringe body 10, any medicinal solution can be used. For example, a high concentration sodium chloride injection solution, minerals, a heparin sodium water solution, nitroglycerin, isosorbide dinitrate, cyclosporine, benzodiazepine-based medical agent, antibiotics, a vitamin preparation (multi vitamin preparation), various amino acids, an antithrombotic drug such as heparin, insulin, antitumor medicine, pain killers, a cardiotonic drug, an intravenous anesthetic, an antiparkinsonism drug, a tumor therapeutic drug, adrenal corticosteroid, a drug for irregular heartbeat, a correction electrolyte, an antiviral drug, and immunomodulator can be used. In addition, medicinal solutions which use continued infinitesimal administration can be used by setting the syringe pump.

In accordance with an aspect, a sealing member 5 is disclosed, which can be a sealing cap or a needle (not shown). For example, known sealing caps or needles can be used.

Figure 18:
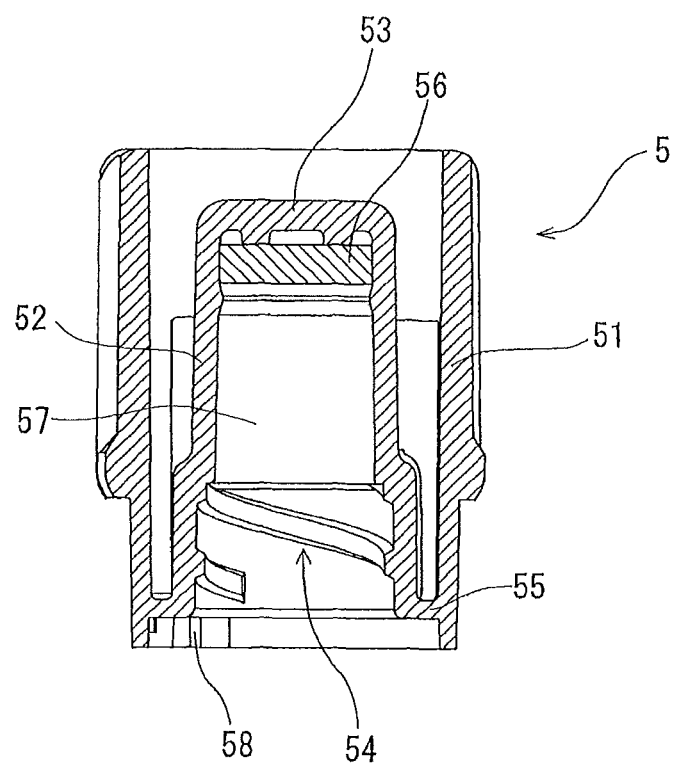
FIG. 18 is a sectional view of a sealing member (sealing cap) for use in the prefilled syringe of the present disclosure.

As shown in FIG. 18, the sealing member 5 of this embodiment is the sealing cap constructed of an inner cylindrical part 52 having an obstruction portion 53, an outer cylindrical part 51 so formed as to surround the inner cylindrical part 52, and a coupling part 55 coupling the inner cylindrical part 52 and the outer cylindrical part 51 to each other. In the sealing member 5, the inner cylindrical part 52 and the outer cylindrical part 51 are integrated with the coupling part 55 on the entire circumference of the proximal end portion thereof.

As shown in FIG. 18, the sealing member 5 has a tip portion accommodation part 57 accommodating a needle-mounting tip portion of the nozzle part 22 of the outer cylinder 2, a cap-side screwing part 54 which screws on the nozzle-side screwing portion 23, and a sealing member 56 which seals the opening formed at the distal end of the tip portion with the sealing member 56 in contact with an aperture plane disposed at the distal end thereof. The proximal end portion of the inner cylindrical part 52 is formed as a columnar space having almost an equal inner diameter. The cap-side screwing part 54 which engages the nozzle-side screwing portion 23 is disposed on the inner surface of the inner cylindrical part 52. In this embodiment, the cap-side screwing part 54 is composed of two spiral portions. By way of example, the materials forming the sealing member can include natural rubber, isoprene rubber, butadiene rubber, fluorine rubber, synthetic rubber such as silicone rubber, thermoplastic elastomers such as olefin-based elastomers, and styrene-based elastomers.

As shown in FIG. 18, in this embodiment, the sealing member 5 has a sealing member-side engaging part 58 which is formed on the inner surface of an opening formed at the proximal end thereof and engageable with the nozzle-side engaging portion 26 of the outer cylinder. The sealing member-side engaging part 58 is constructed of a concave portion formed between two ribs.

As materials forming the sealing cap used as the sealing member 5, various resins such as polypropylene, polyethylene, polystyrene, polyamide, polycarbonate, polyvinyl chloride, poly-(4-methylpentene-1), acrylic resin, acrylonitrile-butadiene-styrene copolymer, polyester such as polyethylene terephthalate, and cyclic polyolefin are listed. By way of example, resins such as the polypropylene and the cyclic polyolefin can be relatively easily molded and are relatively heat-resistant.

According to an aspect, the operation of the prefilled syringe 1 is disclosed below by using FIG. 16.

In the body 10 of the prefilled syringe, the gasket 3 is accommodated in the proximal end portion of the outer cylinder 2. As shown in FIG. 16, the tubular distal end part 42 of the plunger 4 is inserted into the outer cylinder 2 and thereafter enters into the hollow portion of the plunger-mounting member 7 and pressed into the hollow portion of the plunger-mounting member 7. Thereby the outer projection part 43 formed on the outer surface of the tubular distal end part 42 of the plunger 4 presses and elastically deforms the inner projected parts 75a, 75b, 75c, 75d, 75e, and 75f of the plunger-mounting member 7, thus passing through the inner projected parts 75a, 75b, 75c, 75d, 75e, and 75f. Thereafter the inner projected parts 75a, 75b, 75c, 75d, 75e, and 75f are restored to the original configuration thereof or to an almost original configuration thereof. Thereby the proximal end surface of the outer projection part 43 engages the plunger removal prevention locking parts 76a, 76b, 76c, 76d, 76e, and 76f, which helps prevent the plunger 4 from separating from the plunger-mounting member 7. In the plunger 4 of this embodiment, in a state in which the plunger 4 is mounted on the plunger-mounting member 7, the plunger 4 is a little longitudinally movable.

As disclosed above, in the prefilled syringe, the plunger can be mounted on the plunger-mounting member by merely pressing the plunger into the plunger-mounting member without rotating the plunger. Further because the plunger can be relatively smoothly inserted into the plunger-mounting member, it is possible to help restrain an impact from being applied to the gasket body and helps prevent the medicinal solution from leaking when an operation of mounting the plunger on the plunger-mounting member is performed. The plunger mounted on the plunger-mounting member 7 does not separate therefrom. When the plunger mounted on the plunger-mounting member 7 is rotated, there is a possibility that only the plunger 4 rotates inside the plunger-mounting member 7 or the rotation of the plunger 4 causes the plunger-mounting member 7 to rotate. But the rotation of the plunger 4 is not transmitted to the gasket body 6.

The gasket is not limited to the above-disclosed gasket 3, and a gasket 3a as shown in FIGS. 19 through 27 can be used for the prefilled syringe.

The fundamental construction of the gasket 3a is the same as the above-disclosed gasket 3.

The gasket 3a is a tubular body whose distal end is closed and proximal end is open and composed of a gasket body 6a which has the inner cavity 60 extended from the opening formed at the proximal end thereof to the distal end thereof and a plunger-mounting member 7a mounted on the gasket body 6a.

The gasket body 6a has a plunger-mounting member removal prevention rib 83 and a plunger-mounting member movement prevention rib 82 both formed on the inner surface of the inner cavity 60. An annular concave portion is formed between the plunger-mounting member removal prevention rib 83 and the plunger-mounting member movement prevention rib 82.

Figure 19:
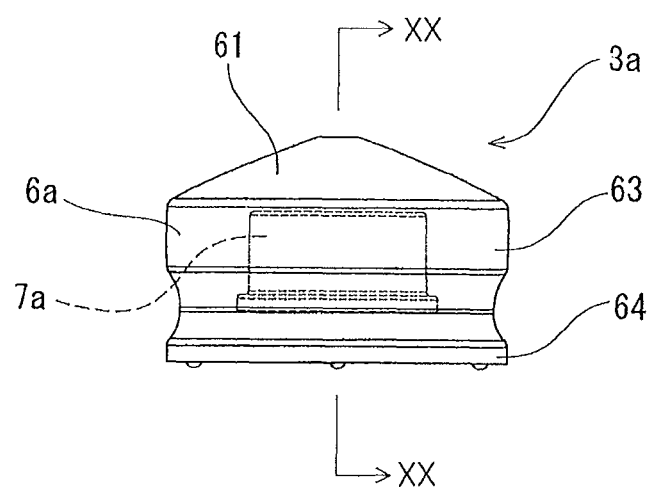
FIG. 19 is an enlarged front view of a gasket for use in a prefilled syringe of another embodiment of the present disclosure.
Figure 20:
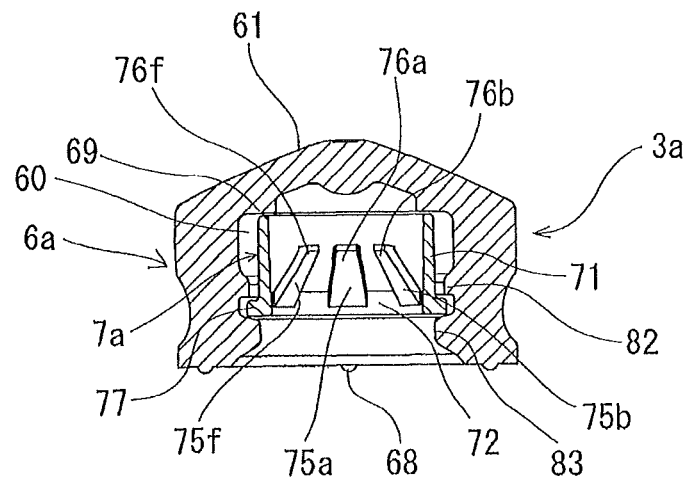
FIG. 20 is a cross-sectional view of the gasket taken along the section line XX-XX in FIG. 19.
Figure 21:
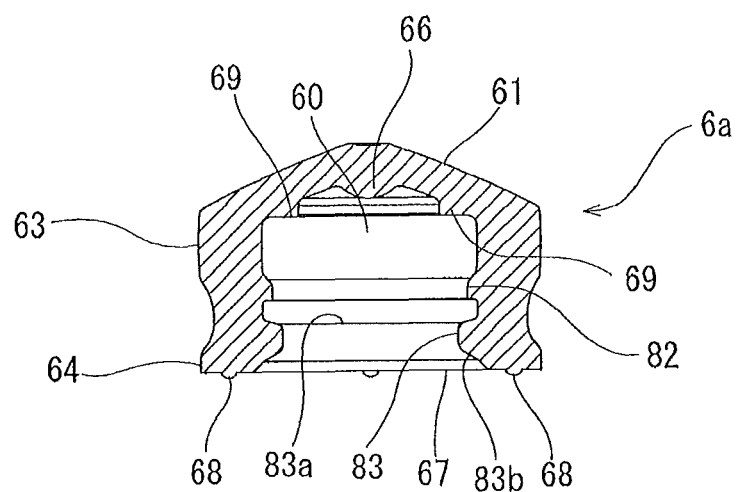
FIG. 21 is a vertical sectional view of a gasket body for use in the gasket shown in FIG. 19.
Figure 22:
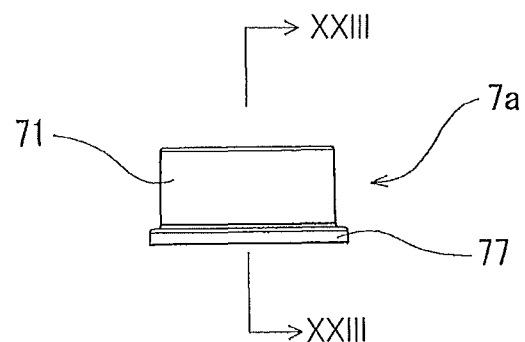
FIG. 22 is a front view of a gasket-mounting member for use in the gasket shown in FIG. 19.
Figure 23:
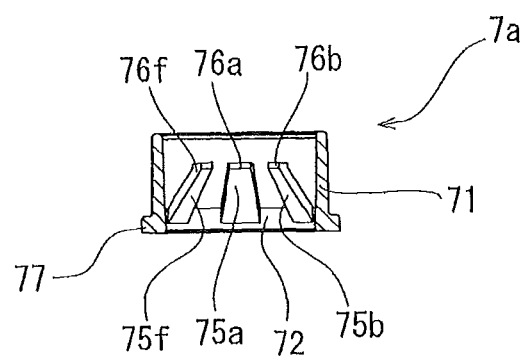
FIG. 23 is a cross-sectional view of the gasket-mounting member taken along the section line XXIII-XXIII in FIG. 22.
Figure 24:
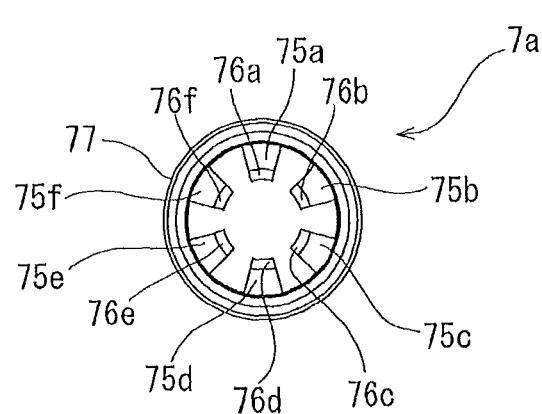
FIG. 24 is a plan view of the gasket-mounting member shown in FIG. 22.
Figure 25:
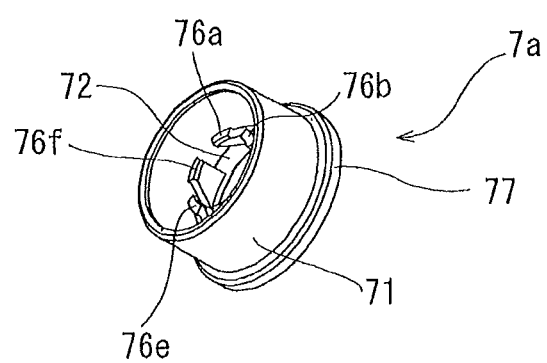
FIG. 25 is a perspective view of the gasket-mounting member shown in FIG. 22 as viewed from a distal side of the gasket-mounting member.
Figure 26:
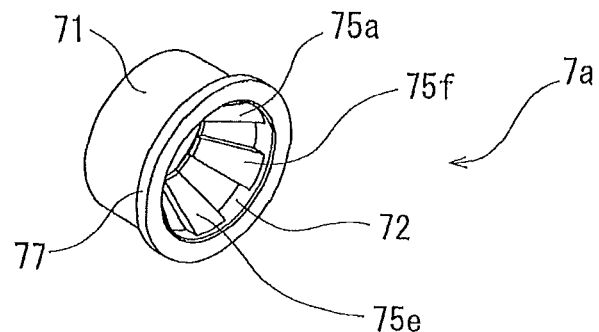
FIG. 26 is a perspective view of the gasket-mounting member shown in FIG. 22 as viewed from a proximal side of the gasket-mounting member.

As shown in FIGS. 19 through 21, the gasket body 6a is the tubular body having the closed distal end and the inner cavity 60 extended from the opening formed at the proximal end thereof toward the distal end thereof. The gasket body 6a has the tapered part 61, the diameter of which taperingly decreases toward the distal end thereof. The gasket body 6a has the distal side annular rib 63 formed at the distal side of the outer surface thereof and the proximal side annular rib 64 formed at the proximal side of the outer surface thereof.

As shown in FIG. 21, the gasket body 6a has the inner cavity 60 which is an accommodation part accommodating the plunger-mounting member 7a. The inner cavity 60 has the plunger-mounting member removal prevention rib 83 and the plunger-mounting member movement prevention rib 82 both formed on the inner surface thereof. In this embodiment, the plunger-mounting member removal prevention rib 83 is disposed at the proximal side (in the vicinity of the opening) of the inner cavity 60, and the plunger-mounting member movement prevention rib 82 is located at a position a little distal from the plunger-mounting member removal prevention rib 83.

The plunger-mounting member removal prevention rib 83 is formed as an endless annular rib almost orthogonal to the axis of the gasket body 6a. By way of example, although the plunger-mounting member removal prevention rib 83 is formed as the annular rib, the plunger-mounting member removal prevention rib 83 may be formed as a plurality of uncontinuous ribs disposed on the same circumference. A distal end surface of the plunger-mounting member removal prevention rib 83 is formed as an annular erect surface 83a erect from the inner surface of the inner cavity 60. A proximal end surface of the plunger-mounting member removal prevention rib 83 is formed as an annular inclined surface 83b, the diameter of which increases toward the proximal end thereof. By way of example, the plunger-mounting member removal prevention rib 83 has an equal inner diameter portion which has a substantially equal inner diameter and is extended in a predetermined length. Because the plunger-mounting member removal prevention rib 83 has the equal inner diameter portion, which helps prevent the plunger-mounting member from separating from the gasket body when the plunger is pulled toward the proximal end thereof. By way of example, the height of the plunger-mounting member removal prevention rib 83 can be about 0.5 to 2.0 mm, for example, about 1.0 to 1.5 mm. The length of the equal inner diameter portion of the plunger-mounting member removal prevention rib 83 can be about 1.0 to 6.0 mm, for example, about 2.0 to 4.0 mm.

In this embodiment, the plunger-mounting member movement prevention rib 82 is located at a position a little proximal from a central portion of the inner cavity 60. The plunger-mounting member movement prevention rib 82 is located at the position a little distal from the plunger-mounting member removal prevention rib 83. As with the removal prevention rib 83, the plunger-mounting member movement prevention rib 82 is formed as an endless annular rib almost orthogonal to the axis of the gasket body 6a. By way of example, the plunger-mounting member movement prevention rib 82 is formed as the annular rib, plunger-mounting member movement prevention rib 82 may be formed as a plurality of uncontinuous ribs disposed on the same circumference. A proximal end surface of the plunger-mounting member movement prevention rib 82 is formed as an annular erect surface erect from the inner surface of the inner cavity 60. A distal end surface of the plunger-mounting member movement prevention rib 82 is formed as an annular inclined surface, the diameter of which increases toward the distal end thereof. By way of example, the plunger-mounting member removal prevention rib 83 has an equal inner diameter portion which has a substantially equal inner diameter and is extended in a predetermined length. The height of the plunger-mounting member movement prevention rib 82 is set a little lower than that of the plunger-mounting member removal prevention rib 83. The height of the plunger-mounting member movement prevention rib 82 can be about 0.3 to 3.0 mm, and for example, about 1.0 to 2.0 mm. The length of the equal inner diameter portion of the plunger-mounting member movement prevention rib 82 can be about 1.0 to 6.0 mm, and for example about 2.0 to 4.0 mm.

In this embodiment, as shown in FIG. 21, the gasket body 6a has the concave portion formed between the plunger-mounting member removal prevention rib 83 and the plunger-mounting member movement prevention rib 82. By way of example, the concave portion is annular. The concave portion (annular concave portion) is capable of accommodating an outer projected part 77 of the plunger-mounting member 7a. The width (length in width direction) of the concave portion (annular concave portion) can be about 1.0 to 6.0 mm.

The gasket body 6a has the projection part 66 projected from the central portion of the inner surface of the distal end portion thereof toward the proximal side thereof. The projection part 66 is capable of contacting the distal end of the tubular distal end part 42 of the plunger 4, when the distal end portion of the gasket body 6a deforms toward its proximal side, thus help preventing the distal end portion of the gasket body 6a from excessively deforming. By way of example, the projection part 66 is approximately semispherical. Generally the diameter of the gasket body 6a is about 5 to 30 mm, and the whole length thereof is about 5 to 30 mm.

As shown in FIG. 21, in this embodiment, the gasket body 6a has a plunger-mounting member contact part 69 on the inner surface of the distal end portion of the inner cavity 60. The plunger-mounting member contact part 69 is formed as an annular surface facing toward the proximal side of the gasket body 6a. As shown in FIG. 20, the distal end surface of the plunger-mounting member 7a is capable of contacting the plunger-mounting member contact part 69. The plunger-mounting member contact part 69 surrounds the projection part 66. By way of example, the plunger-mounting member contact part 69 is formed as the annular surface, the plunger-mounting member contact part 69 may be formed as an annular rib facing the proximal side of the gasket body 6a or as a plurality of uncontinuous ribs facing the proximal side thereof.

By way of example, as constituent materials of the gasket body 6a, the use of the above-disclosed materials disclosed for the gasket body 6. The distal end of the gasket body 6a may be coated with the medical agent low adsorptive substance. As materials forming the medical agent low adsorptive layer, the above-disclosed materials can be used. A lubricant is applied to the outer surface of the gasket body 6*a*. By way of example, the lubricant is applied to at least the surface of the distal side annular rib 63 and that of the proximal side annular rib 64. The lubricant may be applied to the inner surface of the outer cylinder. As the lubricant, silicone oil is suitable. By forming a silicone resin layer on the surface of the gasket body by solidifying the silicone resin, this helps eliminate the need for the use of the lubricant such as the silicone oil.

Figure 27:
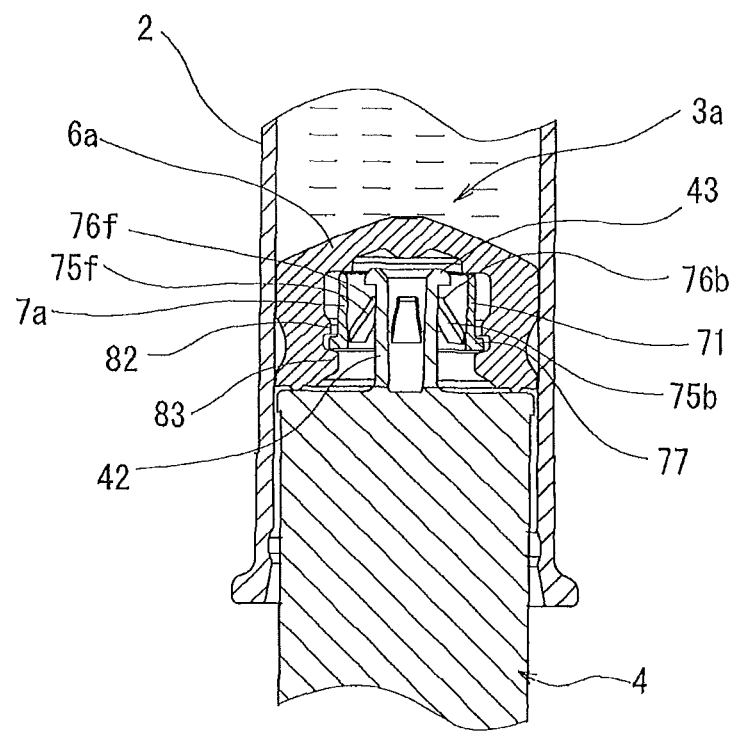
FIG. 27 is an explanatory view for explaining an operation of mounting the plunger on the body of the prefilled syringe of the present disclosure in which the gasket shown in FIG. 19 is used.

As with the above-disclosed plunger-mounting member 7 and as shown in FIGS. 20 through 27, the plunger-mounting member 7*a* is a tubular body having a hollow portion penetrating therethrough from a distal end thereof to a proximal end thereof and can be accommodated inside the inner cavity 60 of the gasket body 6*a*. The plunger-mounting member 7*a* has the outer projected part 77 which is formed on the outer surface thereof and engages the plunger-mounting member removal prevention rib 83 of the gasket body 6*a*, which helps prevent the plunger-mounting member 7*a* from separating from the gasket body 6*a*, a plurality of the elastically deformable inner projected parts 75*a*, 75*b*, 75*c*, 75*d*, 75*e*, and 75*f* which are extended obliquely from an inner portion of a proximal side of the plunger-mounting member 7*a* toward a central and distal end thereof and have a free end respectively at a position which does not reach the center thereof, and a plurality of the plunger removal prevention locking parts 76*a*, 76*b*, 76*c*, 76*d*, 76*e*, and 76*f* formed at the free ends of the inner projected parts 75*a*, 75*b*, 75*c*, 75*d*, 75*e*, and 75*f* respectively. As shown in FIG. 27, the plunger 4 has the pressing part 45 capable of pressing the proximal end portion 67 of the gasket body 6*a* in an operation of mounting the plunger 4 on the gasket 3*a*, the tubular distal end part 42 projected from the pressing part 45 toward the distal end thereof and being capable of penetrating into the plunger-mounting member 7*a*, and the outer projection part 43 which is disposed on the outer surface of the tubular distal end part 42 and engages the plunger removal prevention locking parts 76*a*, 76*b*, 76*c*, 76*d*, 76*e*, and 76*f* of the plunger-mounting member 7*a*. A plurality of ribs 68 is formed on the proximal end surface (proximal end portion) 67 of the gasket body 6*a* of this embodiment.

The outer projected part 77 engages the plunger-mounting member removal prevention rib 83 of the gasket body 6*a*, which helps prevent the plunger-mounting member 7*a* from separating from the gasket body 6*a*. In the plunger-mounting member 7*a* of this embodiment, the outer projected part 77 is formed on the outer surface of the proximal end portion of the body part 71 (specifically, the outer surface of the proximal end of the body part) as an annular projected part almost orthogonal to the axis of the plunger-mounting member 7*a*. The proximal end surface of the outer projected part (annular projected part formed on the outer surface) 73 is formed as an annular erect surface erect from the outer surface of the body part 71. The outer projected part 77 is not limited to the annular configuration, but may be constructed of a plurality of uncontinuous projected parts. The height of the outer projected part 77 can be about 0.5 to 2.0 mm and for example, about 1.0 to 1.5 mm. The outer diameter of the plunger-mounting member 7*a* at the outer projected part 77 thereof is larger than the inner diameter of the plunger-mounting member removal prevention rib 83 of the gasket body 6*a* by about 1.0 to 4.0 mm, and for example, by 2.0 to 3.0 mm.

The plunger-mounting member 7*a* is mounted on the gasket body 6*a* in a state in which the plunger-mounting member removal prevention rib 83 of the gasket body 6*a* and the outer projected part 77 of the plunger-mounting member 7*a* have engaged each other. In this embodiment, the outer projected part 77 of the plunger-mounting member 7*a* is accommodated inside the annular concave portion formed between the plunger-mounting member removal prevention rib 83 and the plunger-mounting member movement prevention rib 82 of a plunger body 3*a*. In the gasket 3*a* of this embodiment, the plunger-mounting member 7*a* is a little movable inside the gasket body 6*a*. But in the gasket 3*a* of the type of this embodiment, the proximal end surface of the outer projected part 77 of the plunger-mounting member 7*a* may contact the distal end surface of the plunger-mounting member removal prevention rib 83, and the distal end surface of the distal end portion of the plunger-mounting member 7*a* may contact the plunger-mounting member contact part 69 of the gasket body 6*a*. For example, the plunger-mounting member 7*a* may be held by the plunger-mounting member contact part 69 of the gasket body 6*a* and the plunger-mounting member removal prevention rib 83, which helps prevent the plunger-mounting member 7*a* from moving inside the gasket body 6*a*. The proximal end of the plunger-mounting member 7*a* mounted on the gasket body 6*a* does not project beyond the gasket body 6*a*. For example, in a state in which the plunger-mounting member 7*a* has been mounted on the gasket body 6*a*, the proximal end of the plunger-mounting member 7*a* is located at a position distal from the proximal end of the gasket body by a predetermined length. As shown in FIG. 27, in a syringe using the gasket 3*a* of this embodiment, when the plunger 4 is mounted on the gasket 3*a*, the distal end of the tubular distal end part 42 of the plunger 4 does not contact the inner surface of the gasket body 6*a*.

As with the plunger-mounting member 7 and as shown in FIGS. 23 through 27, the plunger-mounting member 7*a* has a plurality of the elastically deformable inner projected parts 75*a*, 75*b*, 75*c*, 75*d*, 75*e*, and 75*f* which are extended obliquely from the inner portion of the proximal end 72 of the plunger-mounting member 7*a* (body part 71) toward the central and distal end thereof and have the free end respectively at the position which does not reach the center of the plunger-mounting member 7*a*. There are formed the plunger removal prevention locking parts 76*a*, 76*b*, 76*c*, 76*d*, 76*e*, and 76*f* at the free ends of the inner projected parts 75*a*, 75*b*, 75*c*, 75*d*, 75*e*, and 75*f* respectively. The plunger removal prevention locking parts 76*a*, 76*b*, 76*c*, 76*d*, 76*e*, and 76*f* are engageable with the outer projection part 43 formed on the outer surface of the tubular distal end part 42 of the plunger 4 as disclosed herein later, respectively. The body part 71 is the cylindrical part having an almost equal outer diameter and extending in a predetermined length and accommodating the tubular distal end part 42 of the plunger 4 as disclosed herein later.

In the plunger-mounting member 7*a* of this embodiment, each of the inner projected parts 75*a*, 75*b*, 75*c*, 75*d*, 75*e*, and 75*f* is extended obliquely at a predetermined angle from the inner portion of the proximal end 72 of the plunger-mounting member 7*a* (body part 71) toward the central and distal end thereof. Each of the inner projected parts 75*a*, 75*b*, 75*c*, 75*d*, 75*e*, and 75*f* has the free end at the position which does not reach the center of the plunger-mounting member and becomes smaller toward the free end in the width thereof. In this embodiment, each of the inner projected parts 75*a*, 75*b*, 75*c*, 75*d*, 75*e*, and 75*f* becomes smaller toward the free end in the width thereof.

In the plunger-mounting member 7a of this embodiment, the plunger removal prevention locking parts 76a, 76b, 76c, 76d, 76e, and 76f are formed on the distal end surfaces of the free ends of the inner projected parts 75a, 75b, 75c, 75d, 75e, and 75f of the plunger-mounting member respectively. The plunger removal prevention locking parts 76a, 76b, 76c, 76d, 76e, and 76f are formed as flat surfaces almost orthogonal to the axis of the plunger-mounting member 7a. "Almost orthogonal" as disclosed herein means the concept including inclinations less than ±20 degrees with respect to "orthogonal" (90 degrees). In this embodiment, the plunger removal prevention locking parts 76a, 76b, 76c, 76d, 76e, and 76f incline about 10 degrees with respect to "orthogonal" (90 degrees).

By way of example, at least two inner projected parts almost equiangularly with respect to the axis of the plunger-mounting member 7a are formed. For example, the number of the inner projected parts is four to eight.

Each of the inner projected parts of the plunger-mounting member is elastically deformable. When the inner projected parts are pressed toward the proximal end thereof, the free ends of the inner projected parts deform in a direction in which the free ends become close to the center of the plunger-mounting member. When the inner projected parts are pressed toward the distal end thereof, the free ends deform in a direction in which the free ends become distant from the center of the plunger-mounting member.

In the plunger-mounting member 7a of this embodiment, the proximal end surfaces of a plurality of the inner projected parts 75a, 75b, 75c, 75d, 75e, and 75f of the plunger-mounting member 7a are formed as flat and smooth inclined surfaces inclined toward the center of the plunger-mounting member to form the guide portion for guiding the engagement between the outer projection part of the plunger 4 and the locking parts of the plunger-mounting member. By way of example, the inner surfaces of the free ends of the inner projected parts 75a, 75b, 75c, 75d, 75e, and 75f of the plunger-mounting member 7a form a circular-arc surface whose center almost aligns with the axis of the plunger-mounting member 7a.

As shown in FIG. 27, the plunger-mounting member 7a is mounted on the gasket body 6a in the state in which the plunger-mounting member removal prevention rib 83 of the gasket body 6a and the outer projected part 77 of the plunger-mounting member 7a have engaged each other.

As materials composing the plunger-mounting member 7a, for example, hard resin or the semi-hard resin such as the high-density polyethylene, the polypropylene, the polystyrene, and the polyethylene terephthalate can be used.

The gasket is not limited to the above-disclosed gasket 3, for example, in accordance with another aspect, a gasket 3b as shown in FIGS. 28 through 33 can be used for the prefilled syringe.

In accordance with an embodiment, the fundamental construction of the gasket 3b is the same as the above-disclosed gasket 3.

The gasket 3b is a tubular body having a closed distal end and an open proximal end and has a gasket body 6b which has the inner cavity 60 extended from the opening formed at the proximal end thereof to the distal end thereof and a plunger-mounting member 7b mounted on the gasket body 6b.

The gasket body 6b has the plunger-mounting member removal prevention rib 83 formed on the inner surface of the inner cavity 60.

Figure 28:
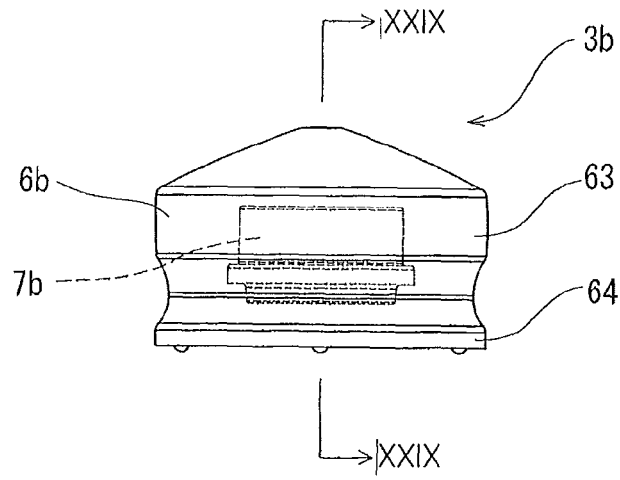
FIG. 28 is an enlarged front view of a gasket for, use in a prefilled syringe of another embodiment of the present disclosure.
Figure 29:
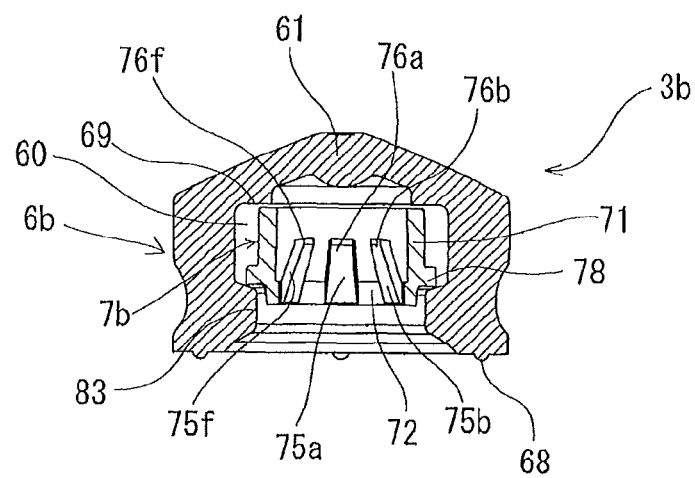
FIG. 29 is a cross-sectional view of the gasket taken along the section line XXIX-XXIX in FIG. 28.
Figure 30:
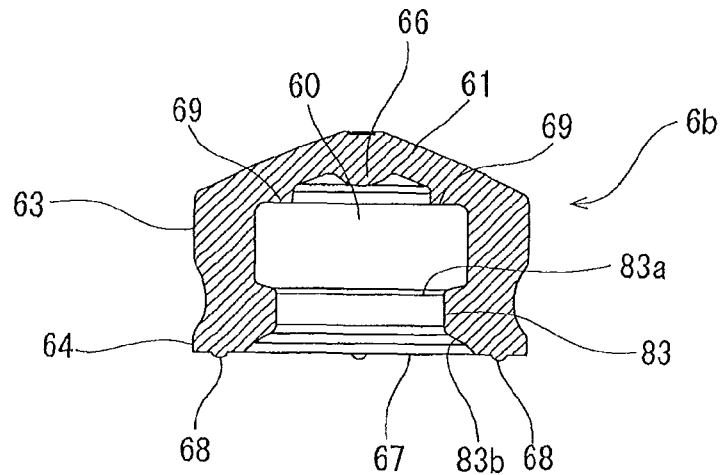
FIG. 30 is a vertical sectional view of a gasket body for use in the gasket shown in FIG. 28.

As shown in FIGS. 28 through 30, the gasket body 6b is the tubular body having the closed distal end and the inner cavity 60 extended from the opening formed at the proximal end of the gasket body 6b toward the distal end thereof. The gasket body 6b has the tapered part 61, the diameter of which taperingly decreases toward the distal end thereof. The gasket body 6b has the distal side annular rib 63 formed at the distal side of the outer surface thereof and the proximal side annular rib 64 formed at the proximal side of the outer surface thereof.

As shown in FIG. 30, the gasket body 6b has the inner cavity 60 which is an accommodation part accommodating the plunger-mounting member 7b. The inner cavity 60 has the plunger-mounting member removal prevention rib 83 formed on the inner surface thereof. In this embodiment, the plunger-mounting member removal prevention rib 83 is disposed at the proximal side (in the vicinity of the opening) of the inner cavity 60. The plunger-mounting member removal prevention rib 83 is formed as an endless annular rib almost orthogonal to the axis of the gasket body 6b. By way of example, the plunger-mounting member removal prevention rib 83 is formed as the annular rib, or the plunger-mounting member removal prevention rib 83 may be formed as a plurality of uncontinuous ribs disposed on the same circumference. The distal end surface of the plunger-mounting member removal prevention rib 83 is formed as the annular erect surface 83a erect from the inner surface of the inner cavity 60. The proximal end surface of the plunger-mounting member removal prevention rib 83 is formed as the annular inclined surface 83b, the diameter of which increases toward the proximal end thereof. By way of example, the plunger-mounting member removal prevention rib 83 has the equal inner diameter portion which has the substantially equal inner diameter and is extended in the predetermined length. Because the plunger-mounting member removal prevention rib 83 has the equal inner diameter portion, it is possible to help prevent the plunger-mounting member from separating from the gasket body when the plunger is pulled toward the proximal end thereof. By way of example, the height of the plunger-mounting member removal prevention rib 83 is about 0.5 to 2.0 mm, and for example, about 1.0 to 1.5 mm. The length of the equal inner diameter portion of the plunger-mounting member removal prevention rib 83 can be about 1.0 to 6.0 mm, and for example, about 2.0 to 4.0 mm.

The gasket body 6b has the projection part 66 projected from the central portion of the inner surface of the distal end portion thereof toward the proximal side thereof. The projection part 66 contacts the distal end of the tubular distal end part 42 of the plunger 4, when the distal end portion of the gasket body 6b deforms toward its proximal side, which helps prevent the distal end portion of the gasket body 6b from excessively deforming. By way of example, the projection part 66 is approximately semispherical. The diameter of the gasket body 6b is about 5 to 30 mm, and the whole length thereof is about 5 to 30 mm.

As shown in FIGS. 29 and 30, in this embodiment, the gasket body 6b has the plunger-mounting member contact part 69 on the inner surface of the distal end portion of the inner cavity 60. The plunger-mounting member contact part 69 is formed as the annular surface facing toward the proximal end of the gasket body 6b. As shown in FIG. 29, the distal end surface of the plunger-mounting member 7b is capable of contacting the plunger-mounting member contact part 69. The plunger-mounting member contact part 69 surrounds the projection part 66. By way of example, the plunger-mounting member contact part is formed as the annular surface, or the plunger-mounting member contact part may be formed as an annular rib facing the proximal side of the gasket body 6b or as a plurality of uncontinuous ribs facing the proximal side thereof.

By way of example, the materials of the gasket body 6b include the above disclosed materials for the gasket body 6. The distal end of the gasket body 6b may be coated with a medical agent low adsorptive substance. As materials forming a medical agent low adsorptive layer, the above-disclosed materials can be used. A lubricant is applied to the outer surface of the gasket body 6b. According to an aspect, the lubricant is applied to at least the surface of the distal side annular rib 63 and that of the proximal side annular rib 64. The lubricant may be applied to the inner surface of the outer cylinder. As the lubricant, silicone oil is suitable. By forming a silicone resin layer on the surface of the gasket body by solidifying the silicone resin, this helps eliminate the need for the use of the lubricant such as the silicone oil.

Figure 31:
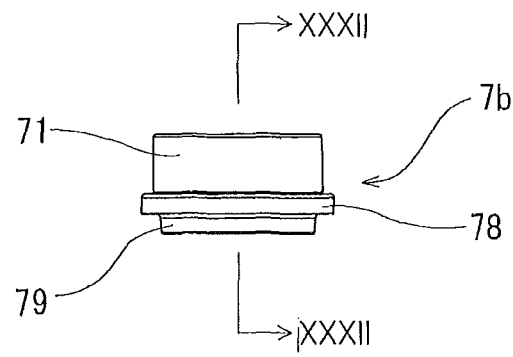
FIG. 31 is a front view of a gasket-mounting member for use in the gasket shown in FIG. 28.
Figure 32:
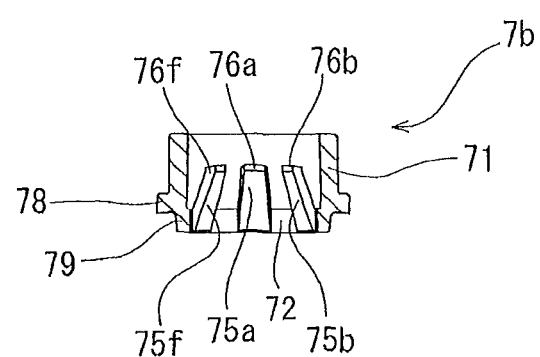
FIG. 32 is a cross-sectional view taken along the section line XXXII-XXXII in FIG. 31.

As with the above-disclosed plunger-mounting member 7 and as shown in FIGS. 31 through 32, the plunger-mounting member 7b is a tubular body having a hollow portion penetrating therethrough from a distal end thereof to a proximal end thereof and can be accommodated inside the inner cavity 60 of the gasket body 6b. The plunger-mounting member 7b has an outer projected part 78 which is formed on an outer surface thereof and engages the plunger-mounting member removal prevention rib 83 of the gasket body 6b, which helps prevent the plunger-mounting member 7b from separating from the gasket body 6b. As with the above-disclosed plunger-mounting members 7 and 7a, the plunger-mounting member 7b has a plurality of the elastically deformable inner projected parts (only 75a, 75b, and 75f are shown) which are extended obliquely from an inner portion of a proximal side of the plunger-mounting member 7b toward a central and distal end thereof and have a free end respectively at a position which does not reach the center thereof, and a plurality of the plunger removal prevention locking parts (only 76a, 76b, and 76f are shown) formed at the free ends of the inner projected parts (only 75a, 75b, and 75f are shown) respectively. A plurality of the inner projected parts and the plunger removal prevention locking parts formed at the free ends of the inner projected parts respectively are the same as those disclosed above.

Figure 33:
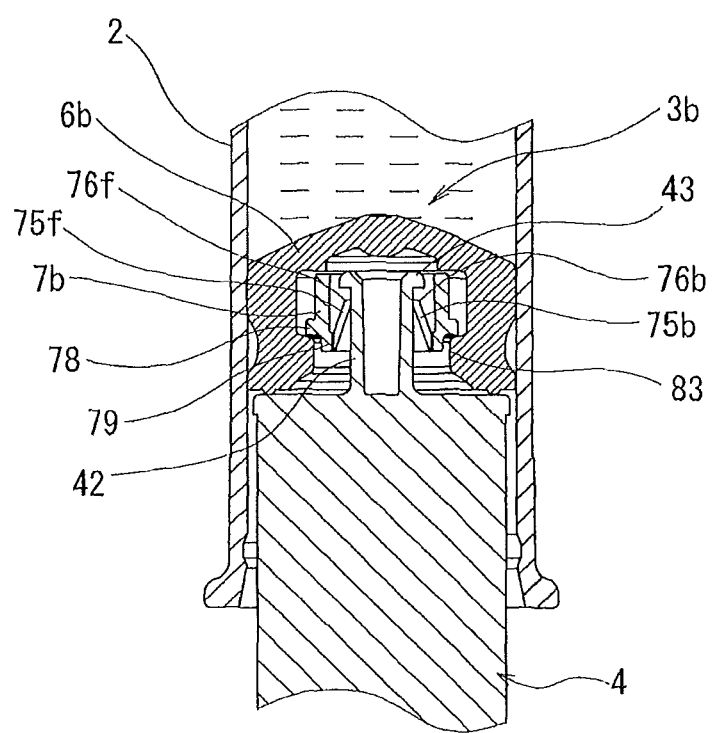
FIG. 33 is an explanatory view for explaining an operation of mounting the plunger on the body of the prefilled syringe of the present disclosure in which the gasket shown in FIG. 28 is used.

As shown in FIG. 33, the plunger 4 has the pressing part 45 capable of pressing the proximal end portion 67 of the gasket body 6b when the plunger 4 is mounted on the gasket 3b, the tubular distal end part 42 projected from the pressing part 45 toward the distal end of the plunger 4 and is capable of penetrating into the plunger-mounting member 7b, and the outer projection part 43 which is disposed on the outer surface of the tubular distal end part 42 and engages the plunger removal prevention locking parts of the plunger-mounting member 7b. A plurality of ribs 68 is formed on the proximal end surface (proximal end portion) 67 of the gasket body 6b of this embodiment.

The outer projected part 78 engages the plunger-mounting member removal prevention rib 83 of the gasket body 6b, which helps prevent the plunger-mounting member 7b from separating from the gasket body 6b. In the plunger-mounting member 7b of this embodiment, the outer projected part 78 is formed on the outer surface of the proximal end portion (specifically, position a little distal from proximal end) of the body part 71 as an annular projected part almost orthogonal to the axis of the plunger-mounting member 7b. A proximal end surface of the outer projected part (annular projected part formed on the outer surface) 78 is formed as an annular erect surface erect from the outer surface of the body part 71. The outer projected part 78 is not limited to the annular configuration, but may be constructed of a plurality of uncontinuous projected parts. The height of the outer projected part 78 can be about 0.5 to 2.0 mm, and for example, about 1.0 to 1.5 mm. The outer diameter of the plunger-mounting member 7b at the outer projected part 78 thereof is larger than the inner diameter of the plunger-mounting member removal prevention rib 83 of the gasket body 6b by about 1.0 to 4.0 mm, and for example, by about 2.0 to 3.0 mm. The gasket body 6b has an annular part 79 projected proximally from the outer projected part 78. The outer surface of the annular part 79 is formed as an annular inclined surface, the diameter of which decreases toward the proximal end thereof.

The plunger-mounting member 7b is mounted on the gasket body 6b in a state in which the plunger-mounting member removal prevention rib 83 of the gasket body 6b and the outer projected part 78 of the plunger-mounting member 7b have engaged each other. In the gasket 3b of this embodiment, the plunger-mounting member 7b is a little movable inside the gasket body 6b. But in the gasket 3b of the type of this embodiment, the proximal end surface of the outer projected part 78 of the plunger-mounting member 7b may contact the distal end surface of the plunger-mounting member removal prevention rib 83, and the distal end surface of the distal end portion of the plunger-mounting member 7b may contact the plunger-mounting member contact part 69 of the gasket body 6b. For example, the plunger-mounting member 7b may be held by the plunger-mounting member contact part 69 of the gasket body 6b and the plunger-mounting member removal prevention rib 83 and prevented from moving inside the gasket body 6b. The proximal end of the plunger-mounting member 7b mounted on the gasket body 6b does not project beyond the gasket body 6b. In a state in which the plunger-mounting member 7b is mounted on the gasket body 6b, the proximal end of the plunger-mounting member 7b is located at a position distal from the proximal end of the gasket body by a predetermined length. As shown in FIG. 33, in a syringe using the gasket 3b of this embodiment, when the plunger 4 is mounted on the gasket 3b, the distal end of the tubular distal end part 42 of the plunger 4 does not contact the inner surface of the gasket body 6b.

As to the material for the plunger-mounting member 7b, the plunger-mounting member 7b can be made of the materials disclosed above.

The gasket is not limited to the above-disclosed gasket 3, and by way of example, a gasket 3c as shown in FIGS. 34 through 39 can be used for the prefilled syringe.

The fundamental construction of the gasket 3c is the same as the above-disclosed gasket 3.

The gasket 3c is a tubular body whose distal end is closed and proximal end is open and includes a gasket body 6c, which has the inner cavity 60 extended from the opening formed at the proximal end thereof to the distal end thereof and a plunger-mounting member 7c mounted on the gasket body 6c.

The gasket body 6c has the plunger-mounting member removal prevention rib 62 formed on the inner surface of the inner cavity 60.

Figure 34:
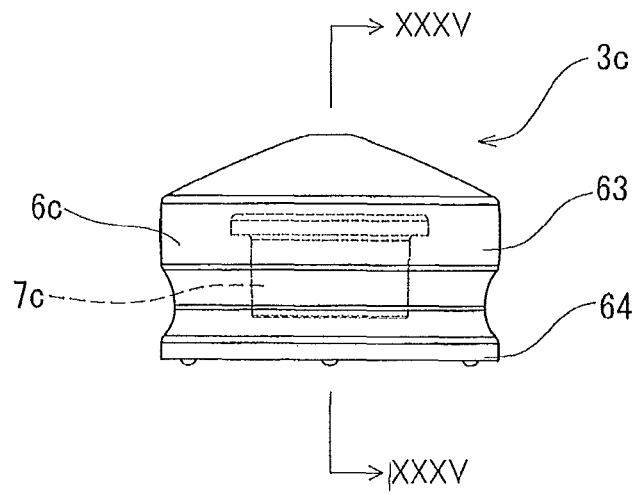
FIG. 34 is an enlarged front view of a gasket for use in a prefilled syringe of another embodiment of the present disclosure.
Figure 35:
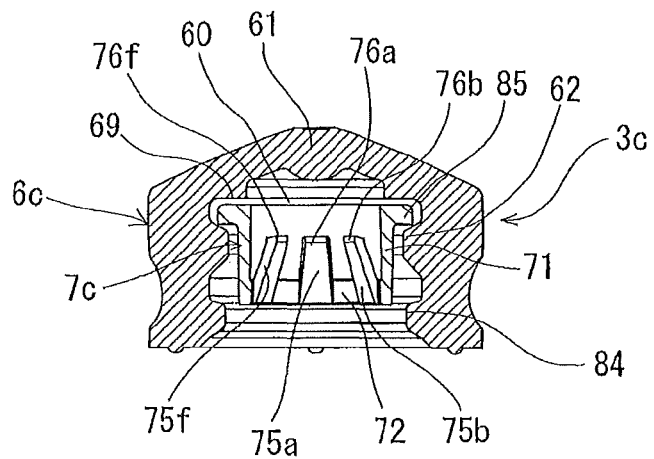
FIG. 35 is a cross-sectional view taken along the section line XXXV-XXXV in FIG. 34.
Figure 36:
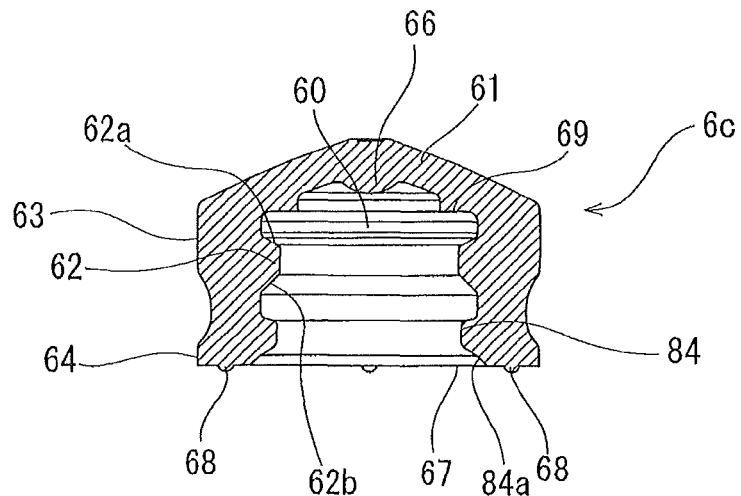
FIG. 36 is a vertical sectional view of a gasket body for use in the gasket shown in FIG. 34.

As shown in FIGS. 34 through 36, the gasket body 6c is the tubular body having the closed distal end and the inner cavity 60 extended from the opening formed at the proximal end of the gasket body 6c toward the distal end thereof. The gasket body 6c has the tapered part 61, the diameter of which taperingly decreases toward the distal end thereof. The gasket body 6c has the distal side annular rib 63 formed at the distal side of the outer surface thereof and the proximal side annular rib 64 formed at the proximal side of the outer surface thereof.

As shown in FIG. 36, the gasket body 6c has the inner cavity 60 which is an accommodation part accommodating the plunger-mounting member 7c. The inner cavity 60 has the plunger-mounting member removal prevention rib 62 formed on the inner surface thereof. In this embodiment, the plunger-mounting member removal prevention rib 62 is disposed at the distal side of the inner cavity 60. The plunger-mounting member removal prevention rib 62 is formed as an endless annular rib almost orthogonal to the axis of the gasket body 6c. By way of example, the plunger-mounting member removal prevention rib 62 is formed as the annular rib, however, the plunger-mounting member removal prevention rib 62 may be formed as a plurality of uncontinuous ribs disposed on the same circumference. The distal end surface of the plunger-mounting member removal prevention rib 62 is formed as an annular inclined surface 62a, the diameter of which increases toward the distal end thereof. By way of example, the plunger-mounting member removal prevention rib 62 has the equal inner diameter portion which has the substantially equal inner diameter and is extended in the predetermined length. Because the plunger-mounting member removal prevention rib 62 has the equal inner diameter portion, this helps prevent the plunger-mounting member from separating from the gasket body, when the plunger is pulled toward the proximal end thereof. The height of the plunger-mounting member removal prevention rib 62 can be about 0.5 to 2.0 mm, and for example, about 1.0 to 1.5 mm. The length of the equal inner diameter portion of the plunger-mounting member removal prevention rib 62 can be about 1.0 to 6.0 mm, and for example, about 2.0 to 4.0 mm.

The gasket 6c of this embodiment has a rib 84 disposed at the proximal side (in the vicinity of the opening) of the inner cavity 60. The rib 84 is formed as an endless annular rib almost orthogonal to the axis of the gasket body 6c. By way of example, the rib 84 is formed as the annular rib, the rib 84 may be formed as a plurality of uncontinuous ribs disposed on the same circumference.

The gasket body 6c has the projection part 66 projected from the central portion of the inner surface of the distal end portion thereof toward the proximal side thereof. The projection part 66 contacts the distal end of the tubular distal end part 42 of the plunger 4, when the distal end portion of the gasket body 6c deforms toward its proximal side, which helps prevent the distal end portion of the gasket body 6c from excessively deforming. By way of example, the projection part 66 is approximately semispherical. The diameter of the gasket body 6c is about 5 to 30 mm, and the whole length thereof is about 5 to 30 mm.

As shown in FIGS. 35 and 36, in this embodiment, the gasket body 6c has the plunger-mounting member contact part 69 on the inner surface of the distal end portion of the inner cavity 60. The plunger-mounting member contact part 69 is formed as an annular surface facing toward the proximal end of the gasket body 6c. As shown in FIG. 35, the distal end surface of the plunger-mounting member 7c is capable of contacting the plunger-mounting member contact part 69. The plunger-mounting member contact part 69 surrounds the projection part 66. By way of example, the plunger-mounting member contact part is formed as the annular surface. The plunger-mounting member contact part may also be formed as an annular rib facing the proximal side of the gasket body 6c or as a plurality of the uncontinuous ribs facing the proximal side thereof.

As constituent materials of the gasket body 6c, the gasket body 6c can be made of the above-disclosed materials as disclosed for the gasket body 6. The distal end of the gasket body 6c may be coated with a medical agent low adsorptive substance. As materials forming a medical agent low adsorptive layer, the above-disclosed materials can be used. A lubricant is applied to the outer surface of the gasket body 6c. The lubricant is applied to at least the surface of the distal side annular rib 63 and that of the proximal side annular rib 64. The lubricant may be applied to the inner surface of the outer cylinder. As to the lubricant, silicone oil is suitable. By forming the silicone resin layer on the surface of the gasket body by solidifying the silicone resin, this helps eliminate the need for the use of the lubricant such as the silicone oil.

Figure 37:
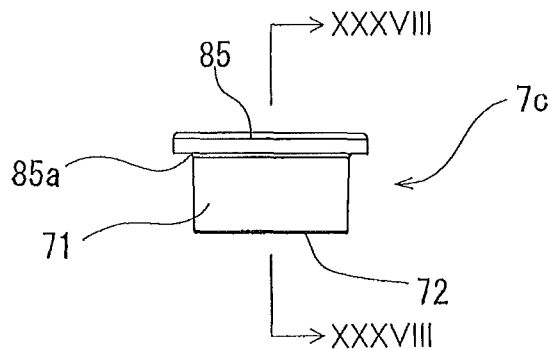
FIG. 37 is a front view of a gasket-mounting member for use in the gasket shown in FIG. 34.
Figure 38:
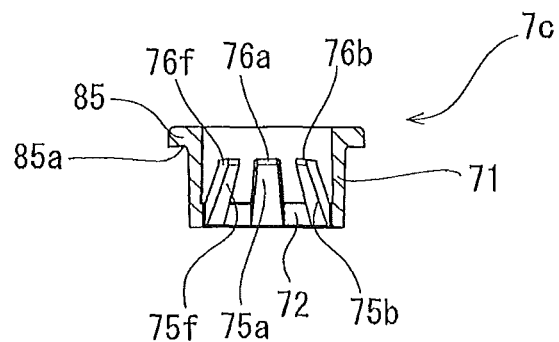
FIG. 38 is a cross-sectional view taken along the section line XXXVIII-XXXVIII in FIG. 37.

As with the above-disclosed plunger-mounting member 7 and as shown in FIGS. 37 through 38, the plunger-mounting member 7c is a tubular body having a hollow portion penetrating therethrough from a distal end thereof to a proximal end thereof and can be accommodated inside the inner cavity 60 of the gasket body 6c. The plunger-mounting member 7c has an outer projected part 85 which is formed on an outer surface thereof and engages the plunger-mounting member removal prevention rib 62 of the gasket body 6c, which helps prevent the plunger-mounting member 7c from separating from the gasket body 6c. As with the above-disclosed plunger-mounting members 7 and 7a, the plunger-mounting member 7c has a plurality of the elastically deformable inner projected parts (only 75a, 75b, and 75f are shown) which are extended obliquely from an inner portion of a proximal side of the plunger-mounting member 7c toward a central and distal end thereof and have a free end respectively at a position which does not reach the center thereof, and the plunger removal prevention locking parts (only 76a, 76b, and 76f are shown) formed at the free ends of the inner projected parts (only 75a, 75b, and 75f are shown) respectively. A plurality of the inner projected parts and the plunger removal prevention locking parts formed at the free ends of the inner projected parts respectively are the same as those disclosed above.

Figure 39:
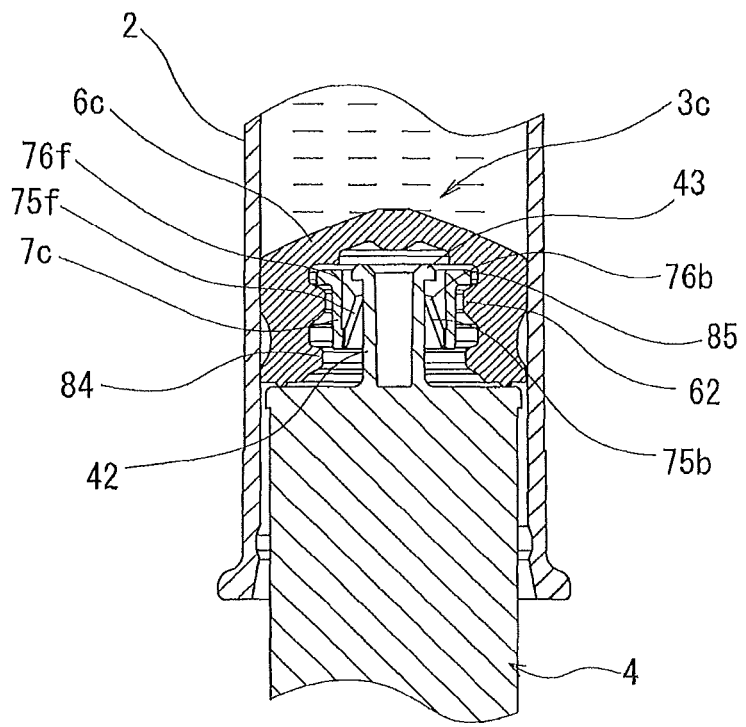
FIG. 39 is an explanatory view for explaining an operation of mounting the plunger on the body of the prefilled syringe of the present disclosure in which the gasket shown in FIG. 34 is used.
Figure 40:
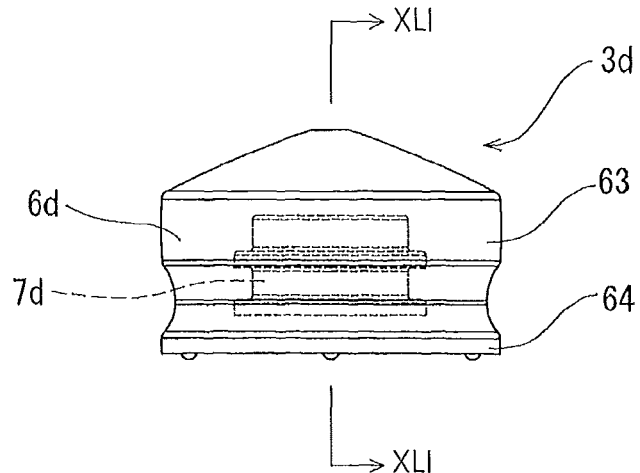
FIG. 40 is an enlarged front view of a gasket for use in a prefilled syringe of another embodiment.

As shown in FIG. 39, the plunger 4 has the pressing part 45 capable of pressing the proximal end portion 67 of the gasket body 6c when the plunger 4 is mounted on the gasket 3c, the tubular distal end part 42 projected from the pressing part 45 toward the distal end of the plunger 4 and being capable of penetrating into the plunger-mounting member 7c, and the outer projection part 43 which is disposed on the outer surface of the tubular distal end part 42 and engages the plunger removal prevention locking parts of the plunger-mounting member 7c. A plurality of the ribs 68 is formed on the proximal end surface (proximal end portion) 67 of the gasket body 6c of this embodiment.

The outer projected part 85 engages the plunger-mounting member removal prevention rib 62 of the gasket body 6c, which helps prevent the plunger-mounting member 7c from separating from the gasket body 6c. In the plunger-mounting member 7c of this embodiment, the outer projected part 85 is formed on the outer surface of the distal end portion (specifically, outer surface of distal end) of the body part 71 as an annular projected part almost orthogonal to the axis of the plunger-mounting member 7c. The outer projected part 85 is not limited to the annular configuration, but may be constructed of a plurality of uncontinuous projected parts. The height of the outer projected part 85 is about 0.5 to 2.0 mm, and for example, about 1.0 to 1.5 mm. The outer diameter of the plunger-mounting member 7c at the outer projected part 85 thereof is larger than the inner diameter of the plunger-mounting member removal prevention rib 62 of the gasket body 6c by about 1.0 to 4.0 mm, and for example, by about 2.0 to 3.0 mm.

The plunger-mounting member 7c is mounted on the gasket body 6c in a state in which the plunger-mounting member removal prevention rib 62 of the gasket body 6c and the outer projected part 85 of the plunger-mounting member 7c have engaged each other. In the gasket 3c of this embodiment, the plunger-mounting member 7c is a little movable inside the gasket body 6c. But the proximal end surface of the outer projected part 85 of the plunger-mounting member 7c may contact the distal end surface of the plunger-mounting member removal prevention rib 62, and the distal end surface of the distal end portion of the plunger-mounting member 7c may contact the plunger-mounting member contact part 69 of the gasket body 6c. By way of example, the plunger-mounting member 7c may be held by the plunger-mounting member contact part 69 of the gasket body 6c and the plunger-mounting member removal prevention rib 62, which helps prevent the plunger-mounting member 7c from moving inside the gasket body 6c. The proximal end of the plunger-mounting member 7c mounted on the gasket body 6c does not project beyond the gasket body 6c. In a state in which the plunger-mounting member 7c is mounted on the gasket body 6c, the proximal end of the plunger-mounting member 7c is located at a position distal from the proximal end of the gasket body by a predetermined length. As shown in FIG. 39, in a syringe using the gasket 3c of this embodiment, when the plunger 4 is mounted on the gasket 3c, the distal end of the tubular distal end part 42 of the plunger 4 does not contact the inner surface of the gasket body 6c.

As the constituent material for the plunger-mounting member 7c, the above-disclosed materials can be used.

The gasket is not limited to the above-disclosed gasket 3, and a gasket 3d as shown in FIGS. 40 through 45 can be used for the prefilled syringe.

The fundamental construction of the gasket 3d is the same as the above-disclosed gasket 3a. The plunger-mounting member to be mounted on the gasket 3d is different from that to be mounted on the gasket 3a. Because the construction of a gasket body 6d is the same as that of the gasket body 6a, reference is made to the above-disclosed.

Figure 41:
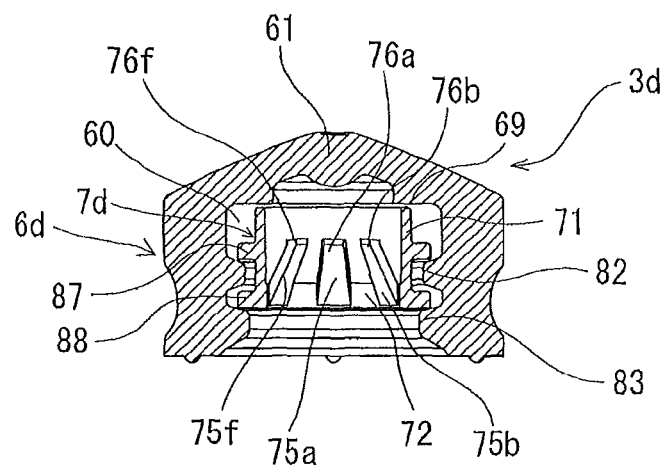
FIG. 41 is a cross-sectional view taken along the section line XLI-XLI in FIG. 40.
Figure 42:
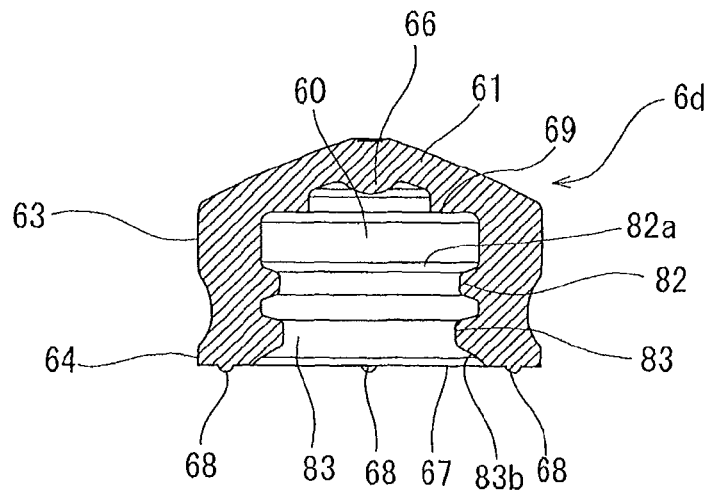
FIG. 42 is a vertical sectional view of a gasket body for use in the gasket shown in FIG. 40.

As with the gasket body 6a and as shown in FIGS. 41 and 42, the gasket body 6d has the inner cavity 60 which is an accommodation part accommodating the plunger-mounting member 7d. The inner cavity 60 has the plunger-mounting member removal prevention rib 83 and the plunger-mounting member movement prevention rib 82 both formed on the inner surface thereof. In this embodiment, the plunger-mounting member removal prevention rib 83 is disposed at the proximal side (in the vicinity of the opening) of the inner cavity 60, and the plunger-mounting member movement prevention rib 82 is located at a position a little distal from the plunger-mounting member removal prevention rib 83. In this embodiment, as shown in FIGS. 41 and 42, the gasket body 6d has the annular concave portion formed between the plunger-mounting member removal prevention rib 83 and the plunger-mounting member movement prevention rib 82. The annular concave portion is capable of accommodating an outer projected part 88 of the plunger-mounting member 7d.

Figure 43:
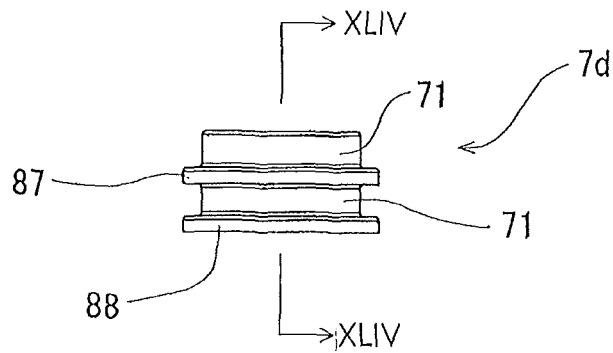
FIG. 43 is a front view of a gasket-mounting member for use in the gasket shown in FIG. 40.
Figure 44:
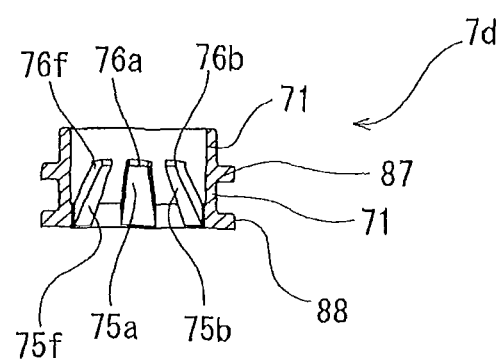
FIG. 44 is a cross-sectional view taken along the section line XLIV-XLIV in FIG. 43.

As with the above-disclosed plunger-mounting member 7 and as shown in FIGS. 43 through 44, the plunger-mounting member 7d is a tubular body having a hollow portion penetrating therethrough from a distal end thereof to a proximal end thereof and can be accommodated inside the inner cavity 60 of the gasket body 6d. The plunger-mounting member 7d has the outer projected part 88 which is formed on an outer surface thereof and engages the plunger-mounting member removal prevention rib 83 of the gasket body 6d, which helps prevent the plunger-mounting member 7d from separating from the gasket body 6d. As with the above-disclosed plunger-mounting members 7 and 7a, the plunger-mounting member 7d has a plurality of the elastically deformable inner projected parts (only 75a, 75b, and 75f are shown) which are extended obliquely from an inner portion of a proximal side of the plunger-mounting member 7d toward a central and distal end thereof and have a free end respectively at a position which does not reach the center thereof, and a plurality of the plunger removal prevention locking parts (only 76a, 76b, and 76f are shown) formed at the free ends of the inner projected parts (only 75a, 75b, and 75f are shown) respectively. A plurality of the inner projected parts and the plunger removal prevention locking parts formed at the free ends of the inner projected parts respectively are the same as those disclosed above.

Figure 45:
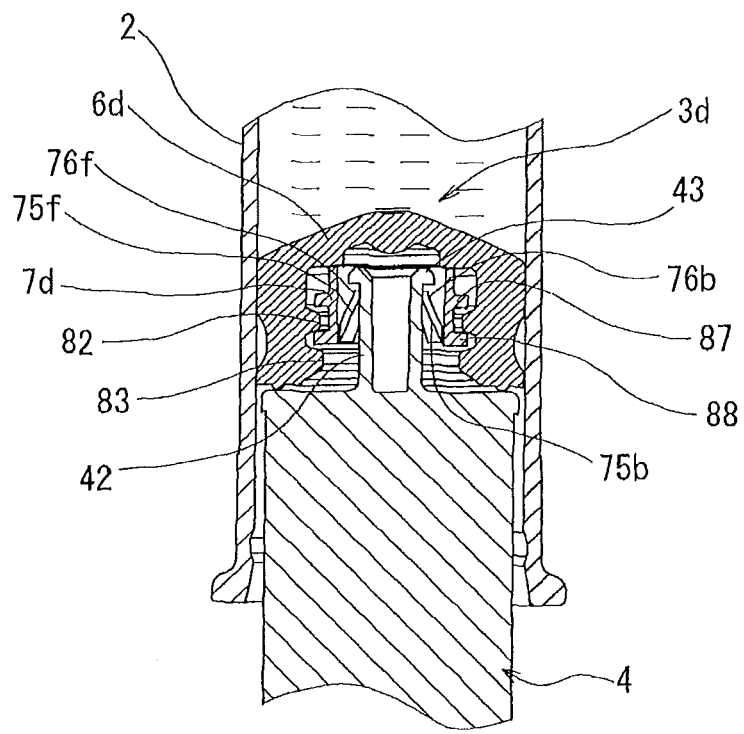
FIG. 45 is an explanatory view for explaining an operation of mounting the plunger on the body of the prefilled syringe of the present disclosure in which the gasket shown in FIG. 40 is used.
Figure 46:
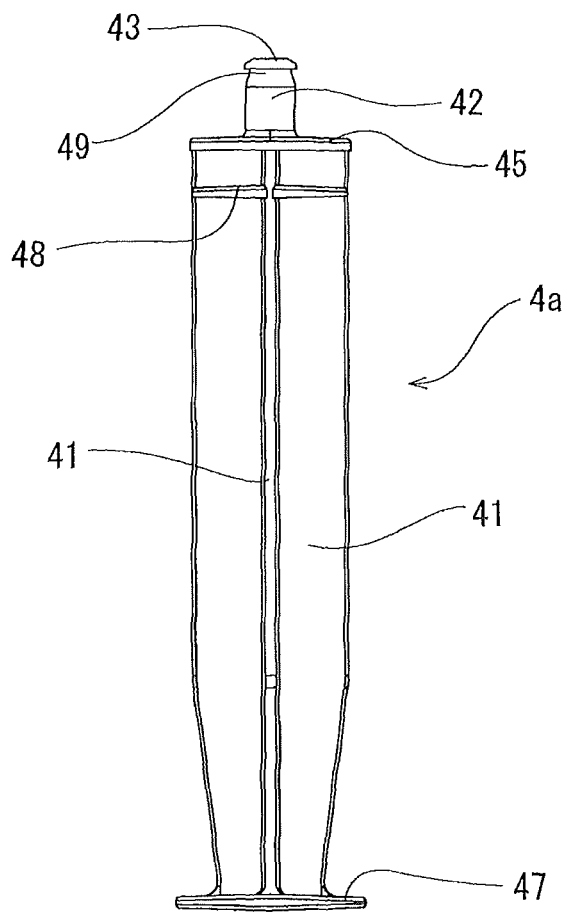
FIG. 46 is an enlarged front view of a plunger for use in a prefilled syringe of another embodiment of the present disclosure.
Figure 47:
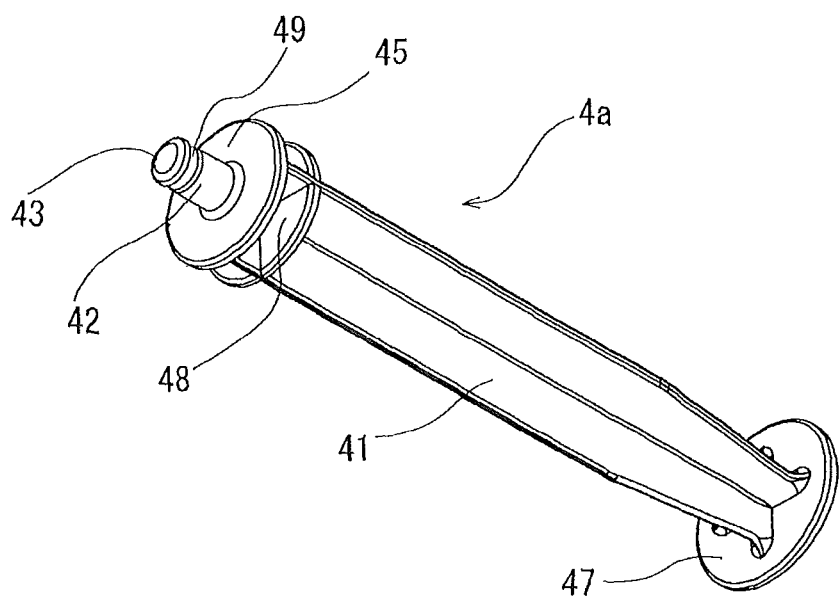
FIG. 47 is a perspective view of the plunger shown in FIG. 46.

As shown in FIG. 45, the plunger 4 has the pressing part 45 capable of pressing the proximal end portion 67 of the gasket body 6d when the plunger 4 is mounted on the gasket 3d, the tubular distal end part 42 projected from the pressing part 45 toward the distal end of the plunger 4 and is capable of penetrating into the plunger-mounting member 7d, and the outer projection part 43 which is disposed on the outer surface of the tubular distal end part 42 and engages the plunger removal prevention locking parts of the plunger-mounting member 7d. A plurality of the ribs 68 is formed on the proximal end surface (proximal end portion) 67 of the gasket body 6d of this embodiment.

The outer projected part 88 engages the plunger-mounting member removal prevention rib 83 of the gasket body 6d, which helps prevent the plunger-mounting member 7d from separating from the gasket body 6d. In the plunger-mounting member 7d of this embodiment, the outer projected part 88 is formed on the outer surface of the proximal end portion (specifically, outer surface of proximal end) of the body part 71 as an annular projected part almost orthogonal to the axis of the plunger-mounting member 7d. The proximal end surface of the outer projected part (annular projected part formed on the outer surface) 88 is formed as an annular erect surface erect from the outer surface of the body part 71. The outer projected part 88 is not limited to the annular configuration, but may be constructed of a plurality of uncontinuous projected parts. By way of example, the height of the outer projected part 88 is about 0.5 to 2.0 mm, and for example, about 1.0 to 1.5 mm. The outer diameter of the plunger-mounting member 7d at the outer projected part 88 thereof is larger than the inner diameter of the plunger-mounting member removal prevention rib 83 of the gasket body 6b by about 1.0 to 4.0 mm, and for example, by about 2.0 to 3.0 mm.

The plunger-mounting member 7d has a second outer projected part 87 formed at a position a little distal from the outer projected part 88. The second outer projected part 87 engages the plunger-mounting member removal prevention rib 82, which helps prevent the plunger-mounting member 7d from moving toward the proximal end thereof. The second outer projected part 87 of the plunger-mounting member 7d is formed as an annular projected part almost orthogonal to the axis of the plunger-mounting member 7d. The proximal end surface of the outer projected part 87 is formed as an annular erect surface erect from the outer surface of the body part 71. The outer projected part 87 is not limited to the annular configuration, and may be constructed of a plurality of uncontinuous projected parts. The height of the outer projected part 87 is about 0.5 to 2.0 mm, and for example, about 1.0 to 1.5 mm. The outer diameter of the plunger-mounting member 7*d* at the outer projected part 87 thereof is larger than the inner diameter of the plunger-mounting member removal prevention rib 82 of the gasket body 6*d* by about 1.0 to 4.0 mm, and for example, by about 2.0 to 3.0 mm.

The plunger-mounting member 7*d* is mounted on the gasket body 6*d* in a state in which the plunger-mounting member removal prevention rib 83 of the gasket body 6*d* and the outer projected part 77 of the plunger-mounting member 7*d* have engaged each other. In the gasket 3*d* of this embodiment, the plunger-mounting member 7*d* is a little movable inside the gasket body 6*d*. But in the gasket 3*d* of the type of this embodiment, the proximal end surface of the outer projected part 88 of the plunger-mounting member 7*d* may contact the distal end surface of the plunger-mounting member removal prevention rib 83, and the distal end surface of the distal end portion of the plunger-mounting member 7*d* may contact the plunger-mounting member contact part 69 of the gasket body 6*d*. For example, the plunger-mounting member 7*d* may be held by the plunger-mounting member contact part 69 of the gasket body 6*d* and the plunger-mounting member removal prevention rib 83, which helps prevent the plunger-mounting member 7*d* from moving inside the gasket body 6*d*. The proximal end of the plunger-mounting member 7*d* mounted on the gasket body 6*d* does not project beyond the gasket body 6*d*. In a state in which the plunger-mounting member 7*d* is mounted on the gasket body 6*d*, the proximal end of the plunger-mounting member 7*d* is located at a position distal from the proximal end of the gasket body by a predetermined length. As shown in FIG. 45, in a syringe using the gasket of this embodiment, when the plunger 4 is mounted on the gasket 3*d*, the distal end of the tubular distal end part 42 of the plunger 4 does not contact the inner surface of the gasket body 6*d*.

As to the material for the plunger-mounting member 7*d*, the above-disclosed material can be used.

The plunger is not limited to the above-disclosed plunger 4, for example, a plunger 4*a* as shown in FIGS. 46 through 50 can be used for the prefilled syringe.

According to an aspect, the plunger 4*a* is different from the above-disclosed plunger 4 in that the former has an annular concave portion 49 formed at the distal end portion 42 thereof. The plunger 4*a* of this embodiment has the concave portion formed at the proximal side of the outer projection part 43 formed on the distal end portion 42. The distal end portions of the inner projected parts of the plunger-mounting member 7 are capable of entering the concave portion. The concave portion is annular.

Figure 48:
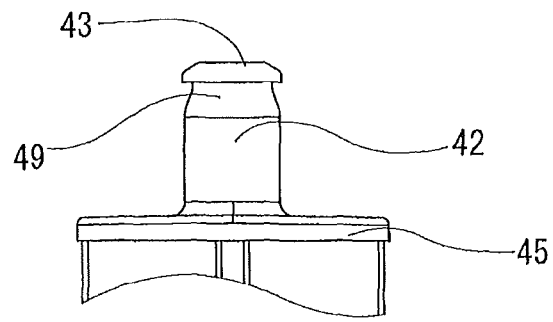
FIG. 48 is an enlarged view of portion of a distal end portion of the plunger shown in FIG. 46.
Figure 49:
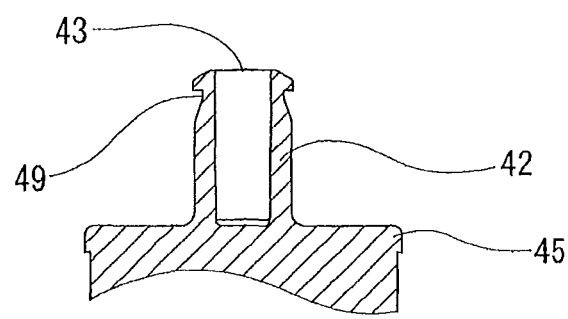
FIG. 49 is an enlarged vertical sectional view of the portion of the distal end portion of the plunger shown in FIG. 46.

As shown in FIGS. 46 through 50 and as with the plunger 4, the plunger 4*a* has the body part 41, the pressing part 45 capable of pressing the proximal end surface of the gasket 3 when the plunger 4*a* is mounted on the gasket 3, the tubular distal end part 42 projected from the pressing part 45 toward the distal end of the plunger 4 and is capable of penetrating into the hollow portion of the plunger-mounting member 7, and the outer projection part 43 which is disposed on the outer surface of the tubular distal end part 42 and engages the plunger removal prevention locking parts (only 76*b* and 76*f* are shown) of the plunger-mounting member 7. The plunger 4*a* has the annular concave portion 49 which is close and back side to the outer projection part 43. The removal prevention parts (only 76*b* and 76*f* are shown) are capable of entering into the annular concave portion 49. As shown in FIGS. 48 and 49, the annular concave portion 49 has a tapered portion which is formed at the proximal end portion thereof and the diameter of which decreases toward the outer projection part 43. By way of example, the depth (depth at the deepest portion) of the annular concave portion 49 is about 0.5 to 3 mm.

Figure 50:
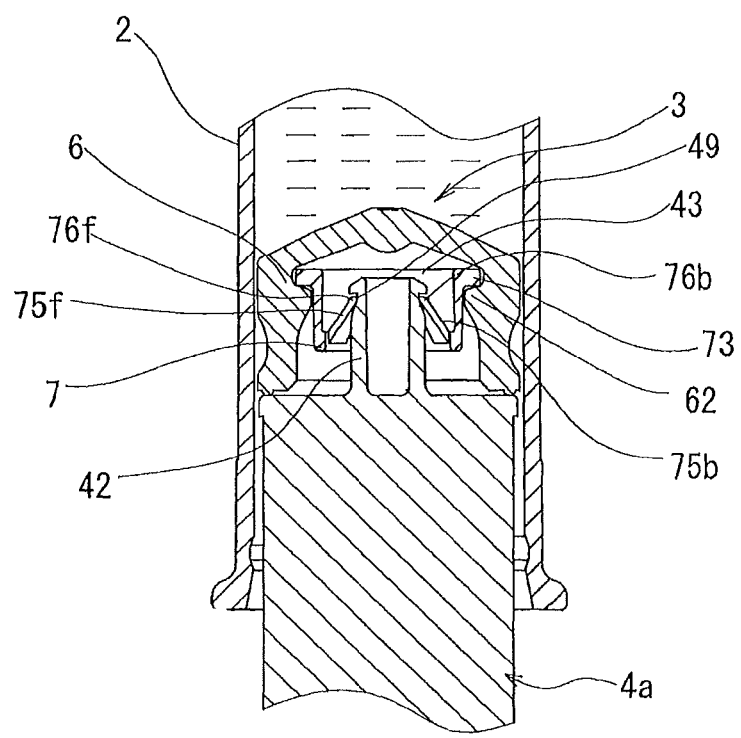
FIG. 50 is an explanatory view for explaining an operation of mounting the plunger on the body of the prefilled syringe of the present disclosure in which the plunger shown in FIG. 46 is used.

The plunger 4*a* can be mounted on the plunger-mounting member 7 by pressing the distal end part 42 into the hollow portion of the plunger-mounting member 7. As shown in FIG. 50, the distal end part 42 of the plunger 4*a* does not contact the inner surface of the gasket body 6, when the plunger 4*a* is mounted on the gasket 3.

In the plunger 4*a* of this embodiment, the outer projection part 43 is formed on the outer surface of the distal end portion (specifically, outer surface of distal end) of the tubular distal end part 42 as the annular outer projection part almost orthogonal to the axis of the tubular distal end part 42 of the plunger 4*a*. The proximal end surface of the outer projection part (annular projection part formed on outer surface) 43 is formed as the annular erect surface erect from the outer surface of the tubular distal end part 42. The outer projection part 43 is not limited to the annular configuration, but may consist of a plurality of the uncontinuous projections. By way of example, the height of the outer projection part 43 is about 0.3 to 1.5 mm, and for example 0.5 to 1.0 mm. The outer diameter of the plunger 4*a* at the outer projection part 43 thereof is larger than the diameter of a circle formed of the inner surfaces of the free ends of the inner projected parts (only 75*b* and 75*f* are shown) of the plunger-mounting member 7 by about 0.5 to 3.0 mm, and for example, by about 1.0 to 2.0 mm.

By pressing the tubular distal end part 42 of the plunger 4*a* including the outer projection part 43 into the hollow portion of the plunger-mounting member 7, the outer projection part 43 presses and elastically deforms the inner projected parts (only 75*b* and 75*f* are shown) of the plunger-mounting member 7 and passes through the inner projected parts (only 75*b* and 75*f* are shown). Thereafter the inner projected parts (only 75*b* and 75*f* are shown) are restored to the original configuration thereof or to an almost original configuration thereof. Thereby the plunger removal prevention locking parts (only 75*b* and 75*f* are shown) enter into the annular concave portion 49 and engage the proximal end surface of the outer projection part 43, which helps prevent the plunger 4*a* from separating from the plunger-mounting member 7.

In the plunger 4*a* of this embodiment, in a state in which the plunger 4*a* is mounted on the plunger-mounting member 7, the inner surface of the free end of each of the inner projected parts (only 75*b* and 75*f* are shown) is in contact with the outer surface of the annular concave portion 49 of the tubular distal end part 42 of the plunger 4*a*. As shown in FIG. 50, in the state in which the plunger 4*a* is mounted on the plunger-mounting member 7, the inner surface of the free end of each of the inner projected parts (only 75*b* and 75*f* are shown) contacts the outer surface of the annular concave portion 49 of the tubular distal end part 42 of the plunger 4*a*. In the state in which the plunger 4*a* is mounted on the plunger-mounting member 7, as shown in FIG. 50, the inner surface of the free end of each of the inner projected parts (only 75*b* and 75*f* are shown) contacts the outer surface (outer surface of the annular concave part 49) of the tubular distal end part 42 of the plunger 4*a* under pressure with the free ends of the inner projected parts being pressed a little in a direction in which the free ends expand a little.

The foregoing embodiments are not intended to restrict the scope of the present invention. Various changes, modifications and equivalents could be effected by one skilled in the art without departing from the spirit and scope of the invention as defined in the appended claims. It is expressly intended that all such changes, modifications and equivalents, which fall within the scope of the claims are embraced by the claims.

What is claimed is:

1. A gasket and plunger assembly for a prefilled syringe comprising:
   a gasket body, the gasket body having a plunger-mounting member removal prevention rib formed on an inner surface of the gasket body;
   a plunger-mounting member; the plunger-mounting member having an outer projected part which engages the plunger-mounting member removal prevention rib of the gasket body;
   at least three elastically deformable inner projected parts which extend obliquely from an inner portion of a proximal side of the plunger-mounting member toward a central and distal end of the plunger-mounting member, and plunger removal prevention locking parts formed at free ends of the inner projected parts; and
   a plunger having a distal end part, which is configured to enter the plunger-mounting member and an outer projection part which engages the plunger removal prevention locking parts of the plunger-mounting member.

2. An assembly according to claim 1, wherein proximal side surfaces of the elastically deformable inner projected parts are formed as flat and smooth inclined surfaces inclined toward a center of the plunger-mounting member to form a guide portion for guiding engagement between the outer projection part of the plunger and the locking parts of the plunger-mounting member.

3. An assembly according to claim 1, wherein when each of the inner projected parts of the plunger-mounting member is pressed toward a proximal side of the plunger-mounting member, the free end of each of the inner projected parts deforms in a direction in which the free end becomes close to the center of the plunger-mounting member.

4. An assembly according to claim 3, wherein a width of the inner projected parts of the plunger-mounting member become smaller toward the free ends of the inner projected parts of the plunger-mounted member.

5. An assembly according to claim 3, wherein
   distal end surfaces of each of the free ends of the inner projected parts of the plunger-mounting member are formed as flat surfaces, which are orthogonal to an axis of the plunger-mounting member;
   the plunger removal prevention locking parts are formed on the distal end surfaces of the free ends; and
   a proximal side surface of the outer projection part of the plunger is formed as a flat surface orthogonal to an axis of the distal end part of the plunger.

6. An assembly according to claim 1, wherein the inner projected parts are formed almost equiangularly with respect to an axis of the plunger-mounting member.

7. An assembly according to claim 1, wherein an inner surface of the free end of each inner projected part of the plunger-mounting member is in contact with an outer surface of the distal end part of the plunger mounted on the gasket.

8. An assembly according to claim 1, wherein a proximal end of the plunger-mounting member does not project beyond the gasket body.

9. An assembly according to claim 1, wherein the distal end part of the plunger is tubular.

10. An assembly according to claim 1, wherein the plunger has a concave portion, formed at a proximal side of the outer projection part, into which distal end portions of the inner projected parts of the plunger-mounting member are capable of entering.

11. A syringe comprising:
    a syringe body having an outer cylinder, a gasket slidably accommodated inside the outer cylinder, and a plunger which is mountable on the gasket;
    wherein the gasket is composed of a gasket body which is a tubular body having a closed distal end and an open proximal end, and having an inner cavity extending from an opening formed at the proximal end of gasket body to the distal end of the gasket body and a plunger-mounting member mounted on the gasket body;
    the gasket body having a plunger-mounting member removal prevention rib formed on an inner surface of the inner cavity;
    the plunger-mounting member formed as a tubular body which has a hollow portion penetrating therethrough from a distal end of the tubular body to a proximal end of the tubular body, and configured to be accommodated inside the inner cavity of the gasket body, the plunger-mounting member having an outer projected part formed on an outer surface of the plunger-mounting member and configured to engage the plunger-mounting member removal prevention rib of the gasket body, a plurality of elastically deformable inner projected parts which are extended obliquely from an inner portion of a proximal side of the plunger-mounting member toward a central and distal end of the plunger-mounting member and each having a free end at a position which does not reach a center of the plunger-mounting member; and plunger removal prevention locking parts formed at the free ends of the inner projected parts;
    the plunger having a pressing part configured to press a proximal end portion of the gasket body in an operation of mounting the plunger on the gasket, a distal end part projecting from the pressing part toward a distal end and configured to enter the plunger-mounting member, and an outer projection part disposed on an outer surface of the distal end part and engaging the plunger removal prevention locking parts of the plunger-mounting member; and
    the plunger-mounting member is mounted on the gasket body in a state in which the plunger-mounting member removal prevention rib of the gasket body and the outer projected part of the plunger-mounting member have engaged each other; and
    wherein when the plunger is mounted on the gasket, the distal end part of the plunger does not contact an inner surface of the gasket body.

12. A syringe according to claim 11, wherein proximal side surfaces of a plurality of the inner projected parts of the plunger-mounting member are formed as flat and smooth inclined surfaces inclined toward the center of the plunger-mounting member to form a guide portion for guiding engagement between the outer projection part of the plunger and the plunger removal prevention locking parts of the plunger-mounting member.

13. A syringe according to claim 11, wherein when each of the inner projected parts of the plunger-mounting member is pressed toward a proximal side of the plunger-mounting member, the free end of each of the inner projected parts deforms in a direction in which the free end becomes close to the center of the plunger-mounting member.

14. A syringe according to claim 13, wherein a width of the inner projected parts of the plunger-mounting member become smaller toward the free ends of the inner projected arts of the plunger-mounted member.

15. A syringe according to claim 13, wherein
distal end surfaces of each of the free ends of the inner projected parts of the plunger-mounting member are formed as flat surfaces respectively orthogonal to an axis of the plunger-mounting member;
the plunger removal prevention locking parts are formed on the distal end surfaces of the free ends respectively; and
a proximal side surface of the outer projection part of the plunger is formed as a flat surface orthogonal to an axis of the distal end part of the plunger.

16. A syringe according to claim 11, wherein a plurality of the inner projected parts are formed almost equiangularly with respect to an axis of the plunger-mounting member; and a number of the inner projected parts to be formed is at least two.

17. A syringe according to claim 11, wherein an inner surface of the free end of each inner projected part of the plunger-mounting member is in contact with an outer surface of the distal end part of the plunger mounted on the gasket.

18. A syringe according to claim 11, wherein the distal end part of the plunger is tubular.

19. A syringe according to claim 11, wherein the plunger has a concave portion, which is formed at a proximal side of the outer projection part, into which distal end portions of the inner projected parts of the plunger-mounting member are capable of entering.

20. A syringe according to claim 11, comprising:
a sealing member which seals an opening formed at a distal end of said outer cylinder, and a medical agent accommodation part formed inside said outer cylinder.

21. A syringe according to claim 20, comprising:
a medical agent accommodated inside the medical agent accommodation part of the outer cylinder of the pre-filled syringe body.

* * * * *

UNITED STATES PATENT AND TRADEMARK OFFICE
CERTIFICATE OF CORRECTION

PATENT NO.         : 9,533,103 B2
APPLICATION NO.    : 13/621112
DATED              : January 3, 2017
INVENTOR(S)        : Okihara Page 1 of 1

It is certified that error appears in the above-identified patent and that said Letters Patent is hereby corrected as shown below:

In the Claims

Column 29, Claim 6, Line 2 change: "are formed almost equiangularly" to -- are formed equiangularly --

Column 31, Claim 14, Line 4 change: "inner projected arts of the" to -- inner projected parts of the --

Column 31, Claim 16, Line 2 change: "are formed almost equiangularly" to -- are formed equiangularly --

Signed and Sealed this
Eighteenth Day of April, 2017

Michelle K. Lee
*Director of the United States Patent and Trademark Office*